(12) United States Patent
Dai et al.

(10) Patent No.: US 9,072,668 B2
(45) Date of Patent: Jul. 7, 2015

(54) NON-AQUEOUS HIGH CONCENTRATION REDUCED VISCOSITY SUSPENSION FORMULATIONS OF ANTIBODIES

(75) Inventors: Weiguo Dai, Radnor, PA (US); Beth Hill, Sunnyvale, CA (US); Kui Liu, Fremont, CA (US); Carl Mieczkowski, Fremont, CA (US)

(73) Assignee: Janssen Biotech, Inc., Horsham, PA (US)

(*) Notice: Subject to any disclaimer, the term of this patent is extended or adjusted under 35 U.S.C. 154(b) by 216 days.

(21) Appl. No.: 13/249,774

(22) Filed: Sep. 30, 2011

(65) Prior Publication Data

US 2012/0076800 A1    Mar. 29, 2012

Related U.S. Application Data

(63) Continuation-in-part of application No. 13/043,925, filed on Mar. 9, 2011.

(60) Provisional application No. 61/311,896, filed on Mar. 9, 2010.

(51) Int. Cl.
| | | |
|---|---|---|
| *A61K 39/395* | (2006.01) | |
| *A61K 39/40* | (2006.01) | |
| *A61K 9/10* | (2006.01) | |
| *A61K 9/00* | (2006.01) | |
| *A61K 9/14* | (2006.01) | |
| *A61K 9/19* | (2006.01) | |
| *A61K 38/38* | (2006.01) | |
| *A61K 47/26* | (2006.01) | |
| *A61K 47/44* | (2006.01) | |
| *C07K 16/24* | (2006.01) | |

(52) U.S. Cl.
CPC ............... *A61K 9/10* (2013.01); *A61K 9/0019* (2013.01); *A61K 9/145* (2013.01); *A61K 9/19* (2013.01); *A61K 38/38* (2013.01); *A61K 47/26* (2013.01); *A61K 47/44* (2013.01); *A61K 39/39591* (2013.01); *C07K 16/241* (2013.01)

(58) Field of Classification Search
None
See application file for complete search history.

(56) References Cited

U.S. PATENT DOCUMENTS

| | | |
|---|---|---|
| 3,639,587 A | 2/1972 | Ames |
| 5,904,935 A | 5/1999 | Eckenhoff et al. |
| 6,719,992 B2 | 4/2004 | Jeng et al. |
| 6,730,328 B2 | 5/2004 | Maskiewicz et al. |
| 7,250,165 B2 | 7/2007 | Heavner et al. |
| 7,666,413 B2 | 2/2010 | Liu et al. |
| 7,740,842 B2 | 6/2010 | Arvinte et al. |
| 2002/0160967 A1 | 10/2002 | Grosse-Bley et al. |
| 2003/0147954 A1 | 8/2003 | Yang et al. |
| 2004/0151779 A1 | 8/2004 | Maskiewicz et al. |
| 2006/0121115 A1 | 6/2006 | Leroux et al. |
| 2006/0142234 A1 | 6/2006 | Chen et al. |
| 2007/0184054 A1 | 8/2007 | Greif et al. |
| 2007/0207210 A1 | 9/2007 | Brown et al. |
| 2008/0226689 A1 | 9/2008 | Berry et al. |
| 2009/0022727 A1 | 1/2009 | Houston et al. |
| 2009/0053169 A1 | 2/2009 | Castillo et al. |
| 2009/0208492 A1 | 8/2009 | O'Connor et al. |
| 2010/0034823 A1 | 2/2010 | Borhani et al. |

FOREIGN PATENT DOCUMENTS

| | | |
|---|---|---|
| EP | 1755650 B1 | 7/2008 |
| WO | WO 2004/089335 A2 | 10/2004 |
| WO | WO 2006/017772 A1 | 2/2006 |
| WO | WO 2006/071693 A2 | 7/2006 |
| WO | WO 2007/125318 A1 | 11/2007 |
| WO | WO 2008/057240 A2 | 5/2008 |
| WO | WO 2010/056657 A8 | 5/2010 |
| WO | WO 2010/146536 A1 | 12/2010 |
| WO | WO 2011/007327 A2 | 1/2011 |

OTHER PUBLICATIONS

Shire, et al., "Challenges in the Development of High Protein Concentration Formulations," American Pharmacists Association Journal of Pharmaceutical Science, 93: 1390-1402 (2004).
Wang, et al., "Antibody Structure, Instability, and Formulation," American Pharmacists Association Journal of Pharmaceutical Science, 96: 1-26 (2007).
"Newtons to Pound-Forces Conversation Calculator," UnitConversion.org, pulled from the Internet Apr. 9, 2012.
PCT International Search Report dated Apr. 18, 2012.
Wicks, et al., "Effect of formulation on the pharmacokinetics and efficacy of doramectin," Veterinary Parasitology, 49: 17-26 (1993).

*Primary Examiner* — Yunsoo Kim
(74) *Attorney, Agent, or Firm* — Kirk Baumeister

(57) ABSTRACT

The present invention relates to non-aqueous high concentration reduced viscosity suspension formulations of antibodies and methods of making and using them.

15 Claims, 22 Drawing Sheets

Figure 10b

```
TVN14   (1)    QVQLVESGGGVVQPGRSLRLSCAASGFTFSSYAMHWVRQAPGKGLEWVAIILYDGSSKRY    (60)
TVN15          QVQLVESGGGVVQPGRSLRLSCAASGFTFSSYAMHWVRQAPGKGLEWVAFILYDGSNKRY
TVN148         QVQLVESGGGVVQPGRSLRLSCAASGFIFSSYAMHWVRQAPGKGLEWVAFMSIDGSNKEY
TVN148B        QVQLVESGGGVVQPGRSLRLSCAASGFIFSSYAMHWVRQAPGKGLEWVAFMSYDGSNKKY
TVN196         QVQLVESGGGVVQPGRSLRLSCAASGFTFSSYAMHWVRQAPGKGLEWVAFISYDGSNKKS
               ***********************  *************:******;: ****.***

TVN14   (61)   ADSVKGRFTISRDNSKNTLYLQMNSLRAEDTAVYYCARDRGISAGGRYYYYGMDVWGQGT   (120)
TVN15          ADSVKGRFTISRDNSKHALYLQMNSLRAEDTAVYYCARDRGVSAGGRYYYYGMDVWGQGT
TVN148         ADSVKGRFTISRDNPKNTLYLQMNSLRAEDTAVYYCARDRGIAAGGRYYYYGMDVWGQGT
TVN148B        ADSVKGRFTISRDNSKNTLYLQMNSLRAEDTAVYYCARDRGIAAGGRYYYYGMDVWGQGT
TVN196         ADSVKGRFTVSRDNSKNTLFLQMNSLRAEDTAVFYCARDRGIGAGGNYYYYGMDVWGQGT
               *****,***,**** *, ,;***************,*******;,********** ***

TVN14  (121)   TVTVSS                                                       (126)
TVN15          TVTVSS
TVN148         TVTVSS
TVN148B        TVTVSS
TVN196         TVTVSS
               ******
```

Figure 12B

```
TNV14   (1)   EIVLTQSPATLSLSPGERATLSCRASQSVBSYLAWYQQKPGQAPRLLIYDASNRATGIPA   (60)
TNV15         EIVLTQSPATLSLSPGERATLSCRASQSVBSYLAWYQQKPGQAPRLLIYDASNRATGIPA
TNV148        EIVLTQSPATLSLSPGERATLSCRASQSVTSYLAWYQQKPGQAPRLLIYDASNRATGIPA
TNV148(B)     EIVLTQSPATLSLSPGERATLSCRASQSVTSYLAWYQQKPGQAPRLLIYDASNRATGIPA
TNV196        EIVLTQSPATLSLSPGERATLSCRASQSVTSYLAWYQQKPGQAPRLLIYDASNRATGIPA
              ****************************** *****************************

TNV14   (61)  RFSGSGSGTDFTLTISSLEPEDFAVYYCQQRSNWPPFTFGPGTKVDIK             (108)
TNV15         RFSGSGSGTDFTLTISSLEPEDFAVYYCQQRSNWPPFTFGPGTKVDIK
TNV148        RFSGSGSGTDFTLTISSLEPEDFAVYYCQQRSNWPPFTFGPGTKVDIK
TNV148(B)     RFSGSGSGTDFTLTISSLEPEDFAVYYCQQRSNWPPFTFGPGTKVDIK
TNV196        RFSGSGSGTDFTLTISSLEPEDFAVYYCQQRSNWPPFTFGPGTKVDIK
              ************************************************
```

NON-AQUEOUS HIGH CONCENTRATION REDUCED VISCOSITY SUSPENSION FORMULATIONS OF ANTIBODIES

CROSS-REFERENCE TO RELATED APPLICATIONS

This application claims is a continuation-in-part of U.S. application Ser. No. 13/043,925, filed 9 Mar. 2011, currently pending, which claims the benefit of U.S. Provisional Patent Application Ser. No. 61/311,896, filed 9 Mar. 2010, the entire contents of which are incorporated herein by reference.

FIELD OF THE INVENTION

The present invention relates to non-aqueous high concentration reduced viscosity suspension formulations and methods of making and using them.

BACKGROUND OF THE INVENTION

Monoclonal antibodies (mAb) have become important protein-based therapeutics for treating various human diseases such as cancer, infectious diseases, inflammation, and autoimmune diseases. Currently, more than 20 monoclonal antibody products have been approved by the Food and Drug Administration, and approximately 20% of all biopharmaceuticals currently being evaluated in clinical trials are monoclonal antibodies (Daugherty et al., Adv. Drug Deliv. Rev. 58:686-706, 2006).

Antibodies can be administered for example via parenteral route, such as by intravenous (IV), subcutaneous (SC) or intramuscular (IM) injection. The SC or IM route reduces the treatment cost and improves convenience for patients and healthcare providers during administration. To be effective and pharmaceutically acceptable, parenteral formulations should preferably be sterile, stable, syringeable, injectable, and nonirritating. These characteristics result in manufacturing, storage, and usage requirements that make injectable formulations difficult dosage forms to develop, in particular formulations having high protein concentrations.

As with any protein therapeutic, antibodies are subject to physical and chemical instability such as aggregation, denaturation, crosslinking, deamidation, isomerization, oxidation and clipping (Wang et al., J. Pharm. Sci. 96:1-26, 2007). Thus, formulation development to identify factors critical for antibody stability is paramount in the development of commercially viable antibody pharmaceuticals.

The required small volumes (typically 0.5-2 mL) for SC or IM injections pose additional formulation challenges as the dosing requires high concentration antibody formulations typically between 100 mg-1 g of protein per dose to achieve therapeutic levels in a patient. The highly concentrated protein formulations often result in increased protein aggregation, poor stability and increased viscosity, impairing injectability and having negative ramifications during process, manufacture, and storage (Shire et al., J. Pharm. Sci. 93:1390-1402, 2004).

Current commercial monoclonal antibody products administered by SC or IM route are usually formulated in aqueous buffers such as phosphate or L-histidine buffer, with excipients or surfactants such as mannitol, sucrose or polysorbate 80 to prevent aggregation and improve stability. Reported antibody concentrations are up to 100 mg/mL in aqueous formulations (Wang et al., J. Pharm. Sci. 96:1-26, 2007). Viscosity of the aqueous formulations has been reduced by addition of salts (U.S. Pat. No. 7,666,413) or organic or inorganic acids (U.S. Pat. No. 7,740,842).

Non-aqueous antibody or protein formulations have been described. WO2006/071693 describes a non-aqueous suspension of up to 100 mg/mL monoclonal antibody in a formulation having a viscosity enhancer (polyvinylpyrrolidone, PVP) and a solvent (benzyl benzoate (BB) or PEG400). WO2004/089335 describes about 100 mg/mL non-aqueous lysozyme suspension formulations containing PVP, glycofurol (GF), BB, benzyl alcohol (BA), or PEG400. US2008/0226689A1 describes a 100 mg/mL human growth hormone (hGH) single phase, three vehicle component (polymer, surfactant and a solvent) non-aqueous viscous formulations. U.S. Pat. No. 6,730,328 describes non-aqueous, hydrophobic, non-polar vehicles of low reactivity (such as perfluorodecalin) for protein formulations. These formulations are non-optimal having, for example, high viscosity that impairs processing, manufacturing and injection, the presence of multiple vehicle components in the formulations, and potential regulatory challenges associated with using not yet approved polymers.

Thus, there is a need to develop improved high concentration non-aqueous formulations.

BRIEF DESCRIPTION OF THE DRAWINGS

FIG. 10. % bioactivity of CNTO148 spray-dried Form-1 formulation of experiment SD_1 in Table 7 and Form-1 100 mg/mL suspension formulations. SD=spray-dried. SO/EO=EO/SO/50/50.

FIG. 12. A) Heavy chain variable region sequences of anti-TNFα antibodies TVN14 (SEQ ID NO:1), TVN15 (SEQ ID NO:2), TVN148 (SEQ ID NO:3), TVN148B (SEQ ID NO:4), and TVN196 (SEQ ID NO: 5) and B) light chain variable region sequences of anti-TNFα antibodies TVN14 (SEQ ID NO:6), TVN15 (SEQ ID NO:6), TVN148 (SEQ ID NO:7), TVN148B (SEQ ID NO:7), and TVN196 (SEQ ID NO: 7).

SUMMARY OF THE INVENTION

Figure 1:
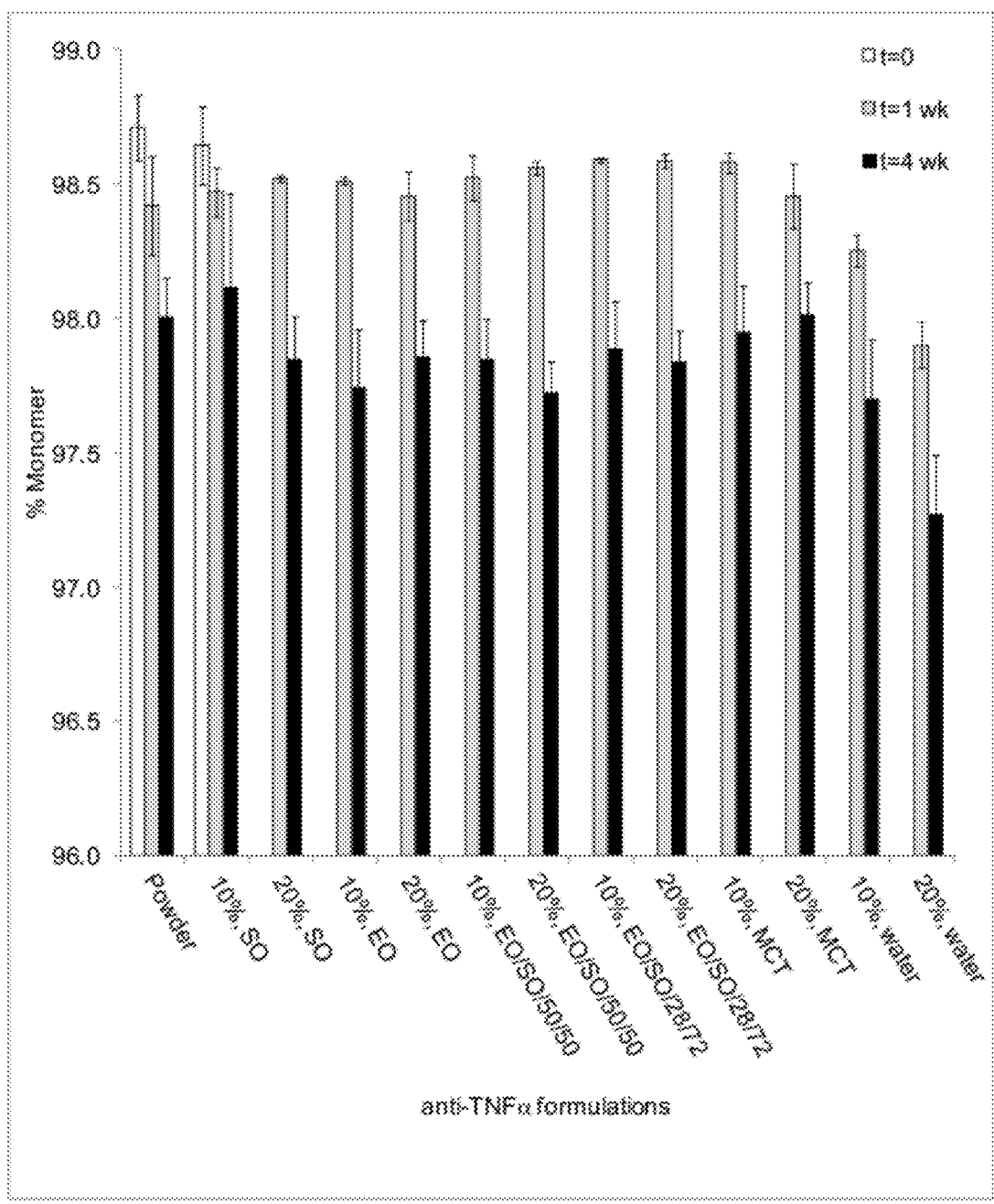
FIG. 1. Stability of anti-TNFα mAb suspension formulations at 1 and 4 weeks of storage at +40° C. Antibody concentrations are indicated in each formulation as % weight (% w/w).
Figure 2A:
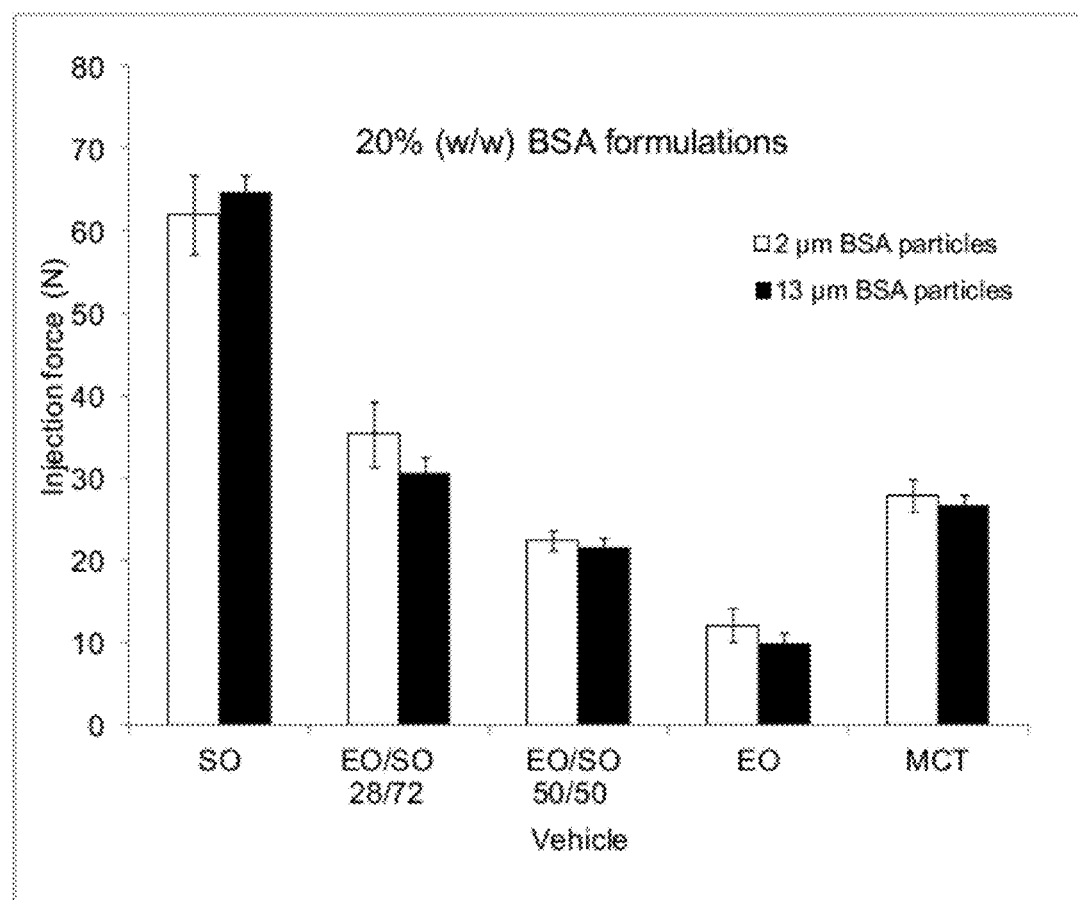
FIG. 2. Injection force (N) of formulations decreases with increasing amount of viscosity reducing agent in a formulation. A. BSA; B. anti-TNFα mAb formulations.
Figure 2B:
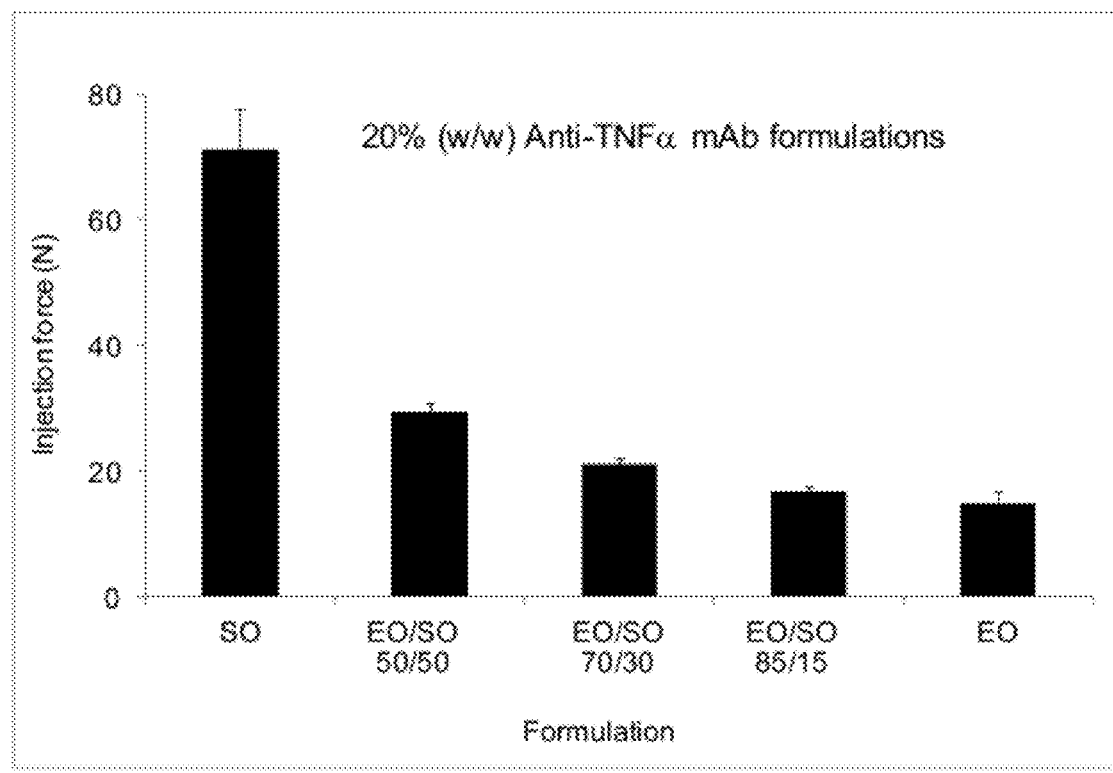
Figure 3A:
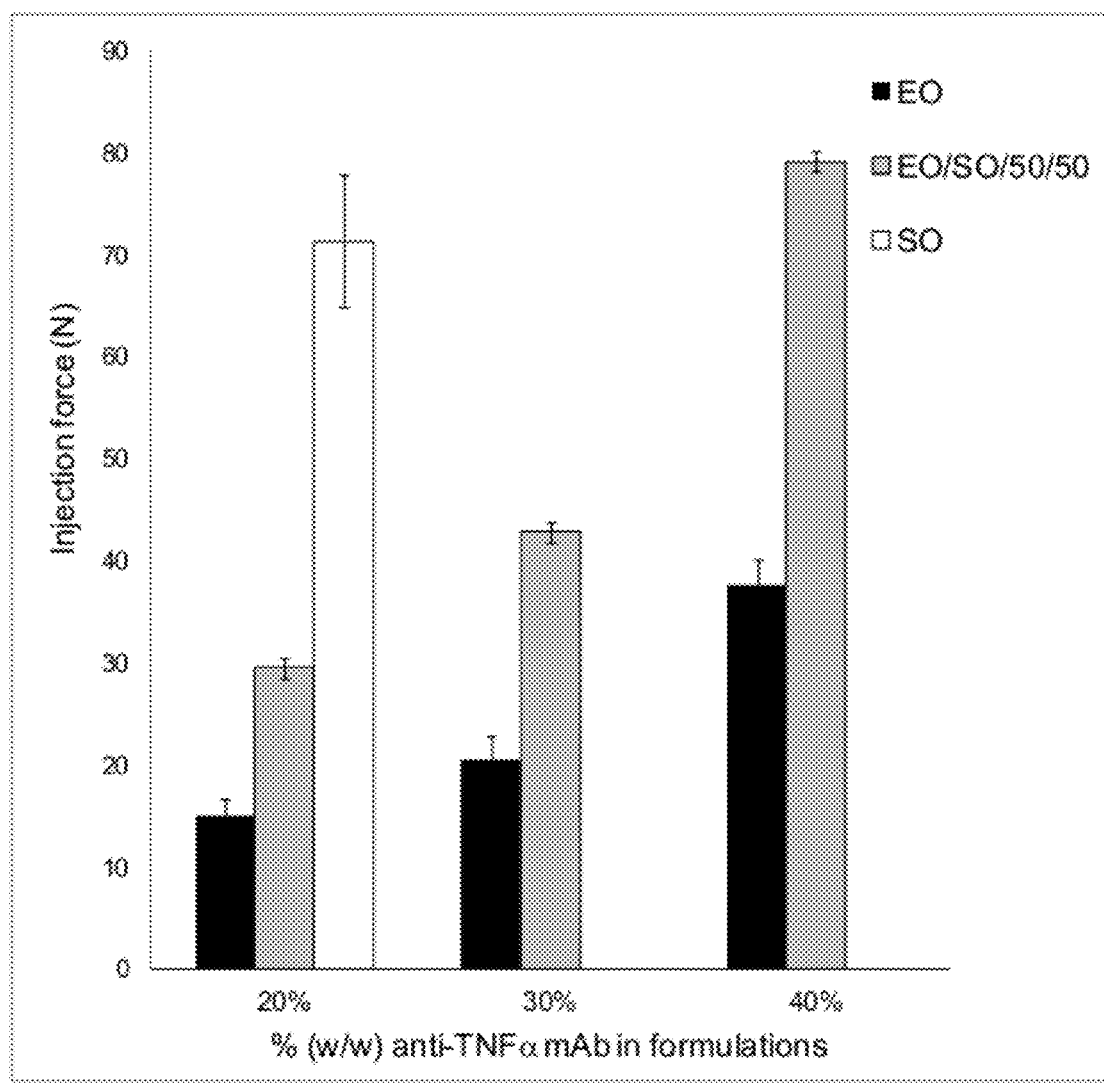
FIG. 3. Injection force and viscosity increase with increasing A. and B. anti-TNFα mAb and C. BSA concentration in the formulations.
Figure 3B:
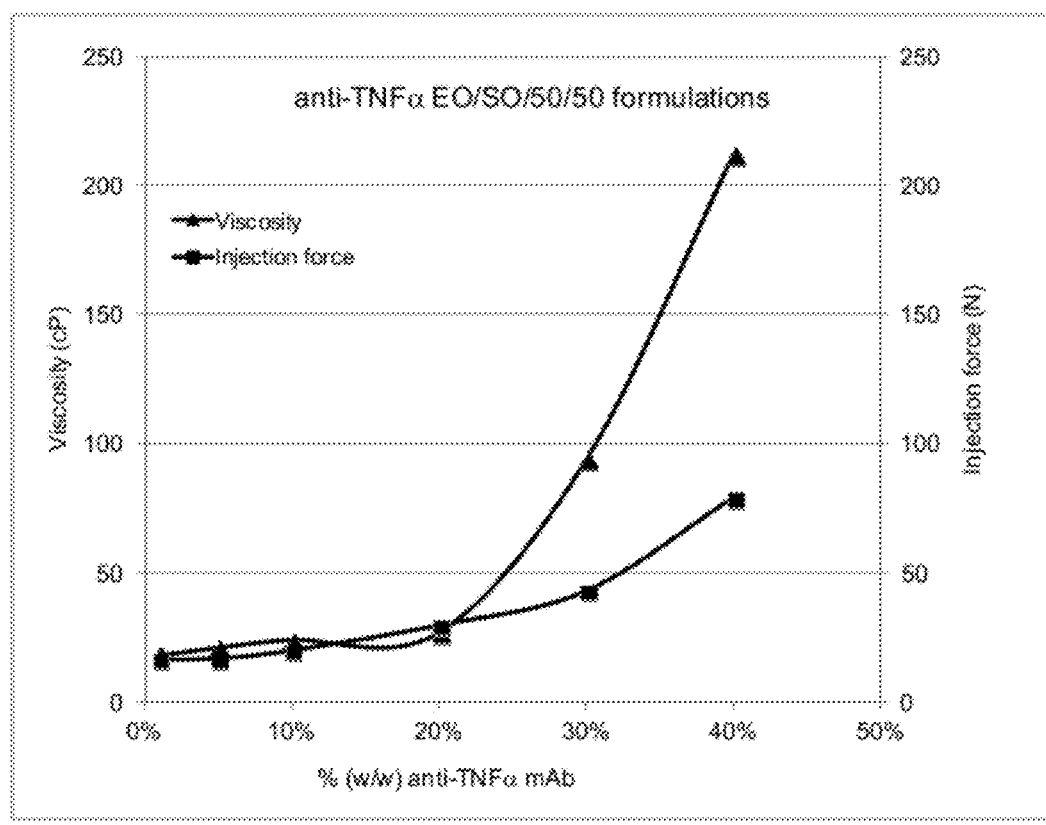
Figure 3C:
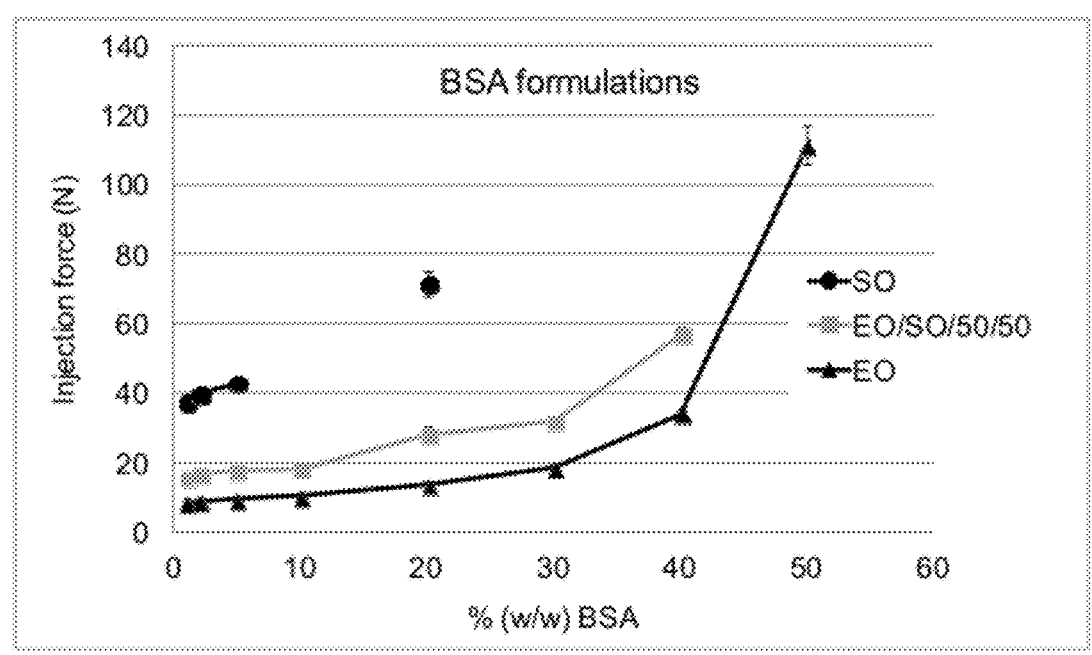

One embodiment of the invention is a non-aqueous high concentration suspension formulation, comprising a vehicle, comprising a hydrophobic agent and a viscosity-reducing agent; and a bioactive molecule.

Another embodiment of the invention is a non-aqueous high concentration suspension formulation, comprising a vehicle comprising sesame oil and ethyl oleate; and a bioactive molecule.

Another embodiment of the invention is a method of reducing an injection force to about 45 Newtons (N) or less of a formulation containing ≥50 mg/ml of a protein in a vehicle comprising a hydrophobic agent, comprising: adding at least 28% by volume of a viscosity reducing agent into the vehicle comprising a hydrophobic agent; or utilizing protein particles having particle size between about 2 μm-13 μm to prepare the formulation, wherein the injection force is measured using a 1 mL rigid needle shield glass syringe having a 0.25 inch inside diameter, equipped with a 0.5 inch 26½-gauge needle at a 250 mm/min. injection speed.

Another embodiment of the invention is a method of making a non-aqueous high concentration suspension formulation of a bioactive molecule, comprising providing a bioactive molecule; providing a hydrophobic agent; providing a viscosity reducing agent; mixing the hydrophobic agent and the viscosity reducing agent to form a vehicle; and adding the bioactive molecule into the vehicle formed

DETAILED DESCRIPTION OF THE INVENTION

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

"A hydrophobic agent" as used herein refers to a material having a hydrophilic-lipophilic balance (HLB) value of 0-13. Exemplary hydrophobic agents are vegetable oils, fatty acids having 8-24 carbons, wax, biodegradable polymers, and amphiphilic materials. Exemplary vegetable oils are almond oil, anise oil, apricot kernel oil, arachis oil, argan oil, avocado oil, borage oil, cajuput oil, canola oil, caraway oil, *cassia* oil, castor oil, cinnamon oil, citronella oil, clove oil, coconut oil, coriander oil, corn oil, cottonseed oil, eucalyptus oil, evening primrose oil, fennel oil, geranium oil, grapeseed oil, hazelnut oil, hemp oil, jojoba oil, juniper oil, lavender oil, lemon oil, *macadamia* oil, mace oil, melaleuca oil, neem oil, neroli oil, niaouli oil, nutmeg oil, olive oil, orange oil, palm oil, palm kernel oil, pine oil, poppyseed oil, pulegium oil, pumpkin seed oil, rapeseed oil, rice bran oil, rosehip oil, rosemary oil, rue oil, safflower oil, sesame oil (SO), spearmint oil, soybean oil, sunflower oil, thyme oil, walnut oil or wheatgerm oil. Exemplary fatty acids are caprylic acid, capric acid, lauric acid, myristic acid, palmitic acid, stearic acid, arachidic acid, linoleic acid, myristoleic acid, palmitoleic acid, sapienic acid, oleic acid, α-linolenic acid, arachidonic acid, eicosapentaenoic acid, erucic acid, docosahexaenoic acid, eicosapentaenoic acid, docosahexaenoic acid, docosapentaenoic acid, and glyceride (monoglyceride; diglyceride; triglyceride) with different chain lengths. Exemplary biodegradable polymers are polylactic acid (PLA), polyglycolic acid (PGA), polylactic-co-glycolic acid (PLGA), poly ε-caprolactone (PCL), polyorthoesters, polyhydroxybutyrate (PHB), polydioxanone, polyanhydrides, polytrimethylene carbonate, and polyphosphazenes. Exemplary amphiphilic materials are a polyethoxylated castor oil or derivative thereof (collectively referred to as a "polyethoxylated castor oil"), a polyoxyethylene alkyl ether, a polyoxyethylene sorbitan fatty acid ester, a polyoxyethylene stearate, a block copolymer of polyethylene oxide ("PEO")-polypropylene oxide ("PPO")—PEO, a block copolymer of PPO-PEO-PPO, a tetra-functional block copolymer of PEO-PPO, such as $(PEO-PPO)_2$—$(PPO-PEO)_2$, or a tetra-functional block copolymer of PPO-PEO, such as $(PPO-PEO)_2$—$(PEO-PPO)_2$. Exemplary hydrophobic agents and their characteristics are shown in Table 1. The viscosities are measured at 25° C. unless noted in the parenthesis.

Figure 4A:
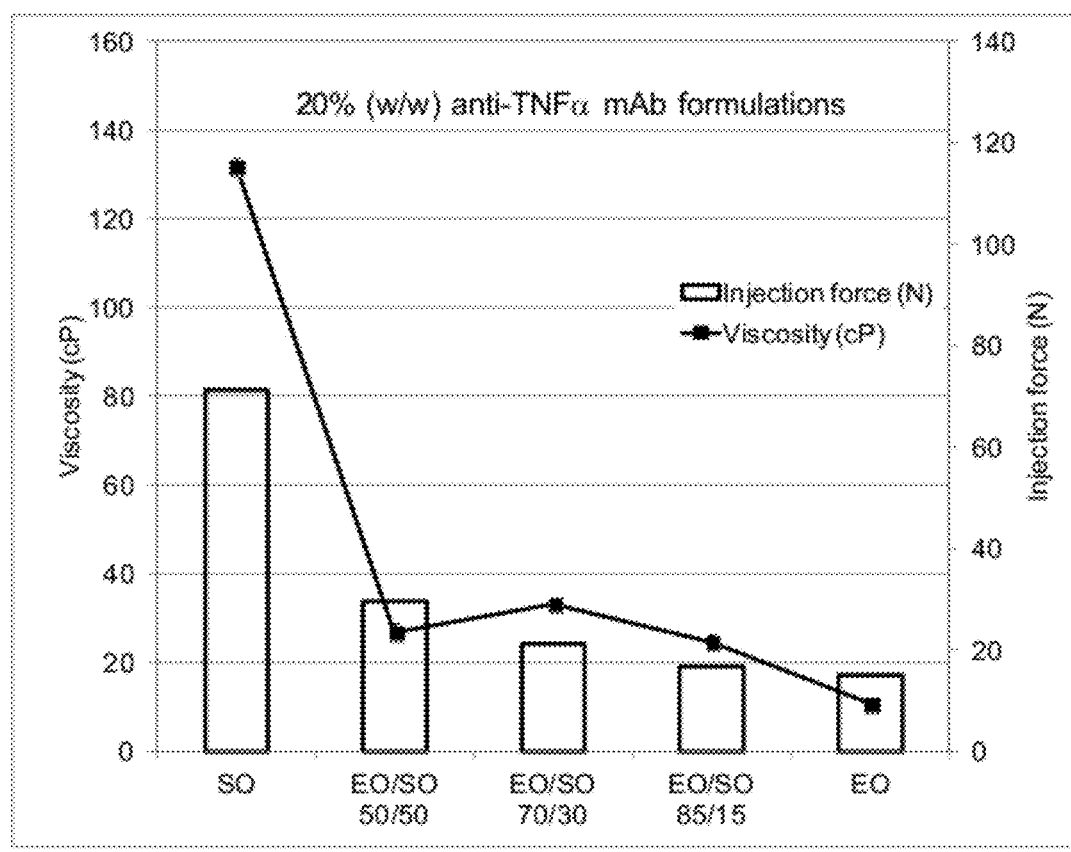
FIG. 4. Correlation between injection force and viscosity of anti-TNFα mAb formulations. A. formulations with 20% anti-TNFαmAb; B. all anti-TNFαmAb formulations studied.
Figure 4B:
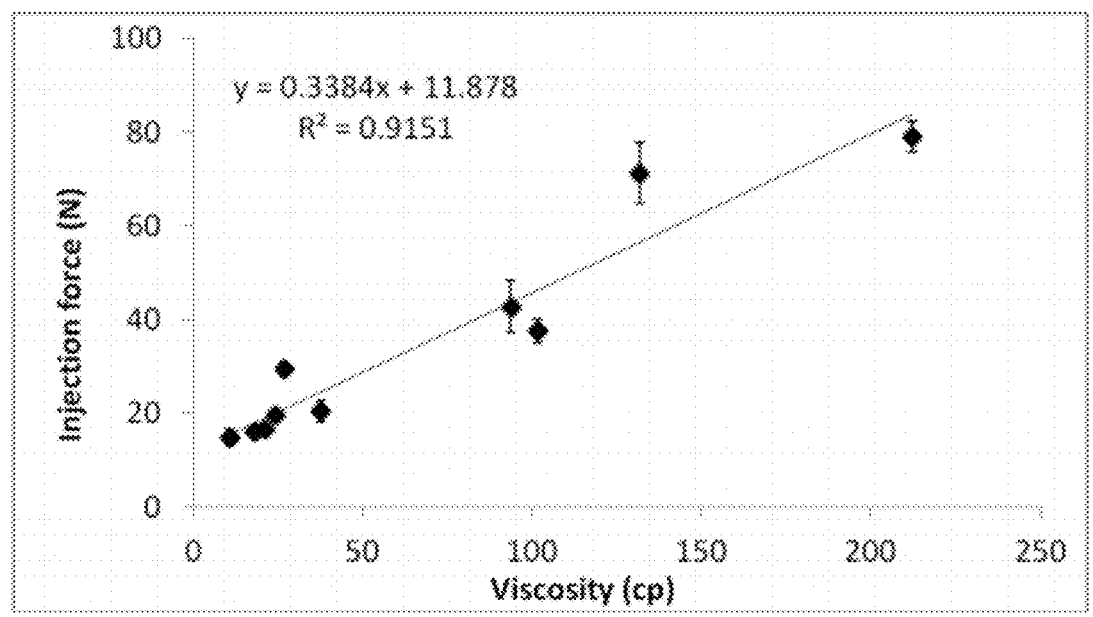
Figure 5:
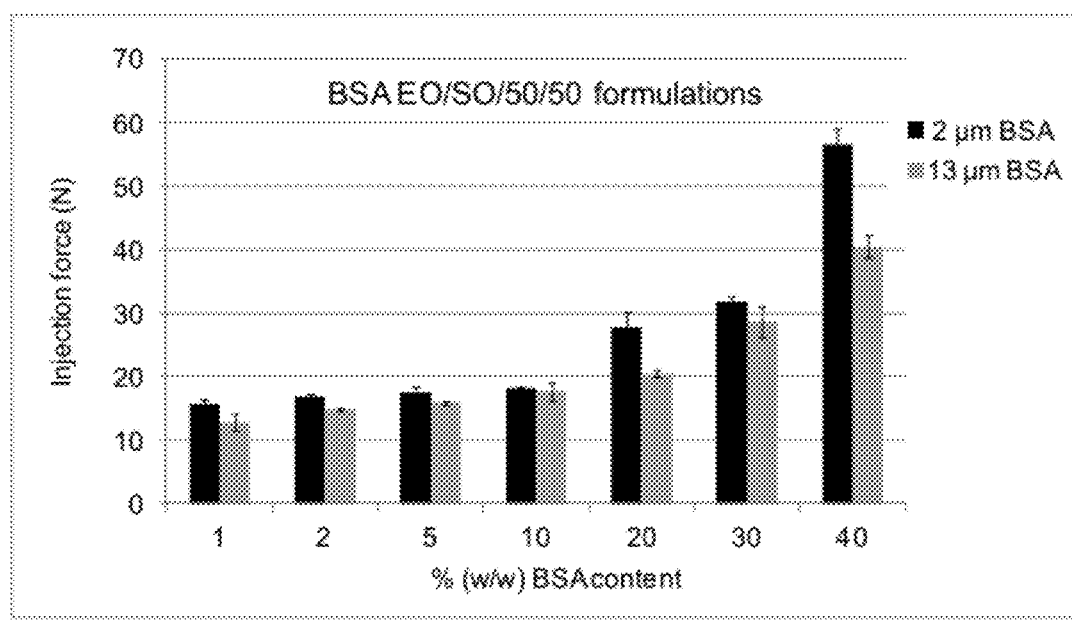
FIG. 5. Dependence of injection force on protein concentration and particle size in the formulation. Vehicle: Ethyl Oleate (EO)/Sesame Oil (SO)/50/50.
Figure 6A:
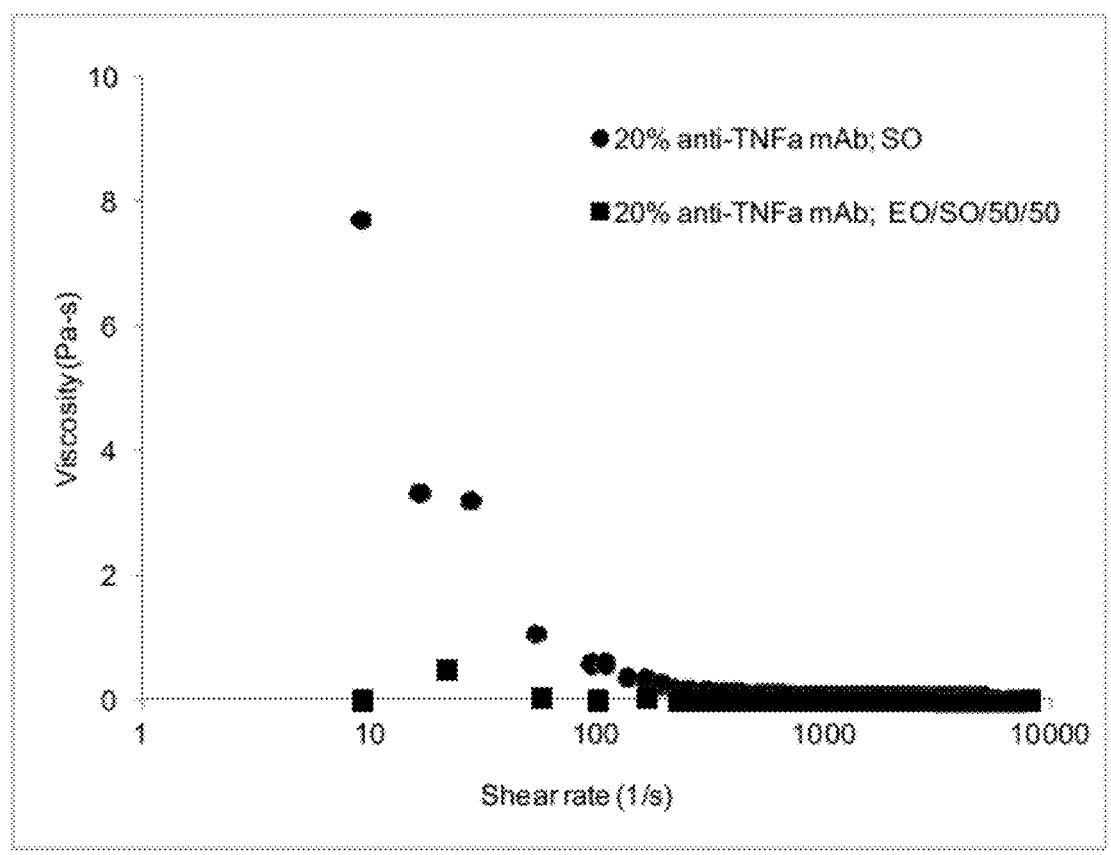
FIG. 6. A. Increasing shear rate can reduce viscosity of high concentration protein formulations. A. Vehicle choice affects dependence of viscosity on shear rate. B. Protein concentration affects dependence of viscosity on shear rate. Anti-TNFα mAb EO/SO/50/50 formulations.
Figure 6B:
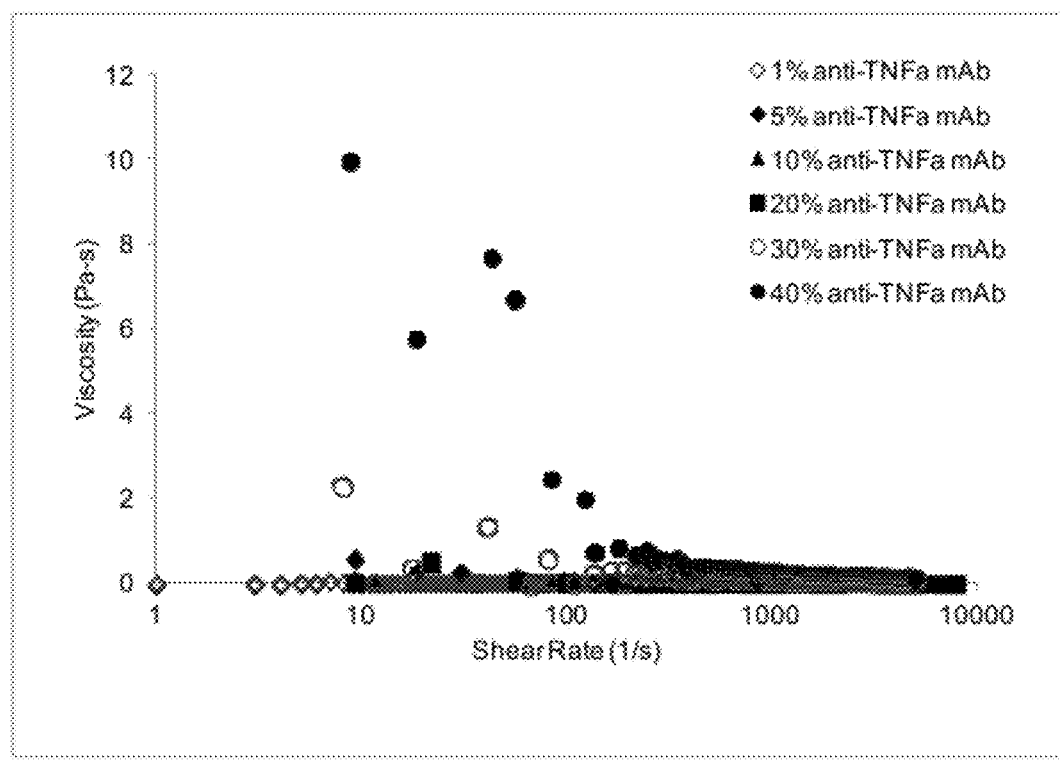

The term "viscosity" as used herein is a measure of fluid resistance to flow. Viscosity may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. The dimension of kinematic viscosity is $L^2/T$ where L is a length and T is a time. Commonly, kinematic viscosity is expressed in centistokes (cSt). The International System of Units (SI) unit of kinematic viscosity is $mm^2/s$, which is 1 cSt. "Absolute viscosity", sometimes called "dynamic" or "simple viscosity", is the product of kinematic viscosity and fluid density. Absolute viscosity is expressed in units of centipoise (cP). The SI unit of absolute viscosity is the millipascal-second (mPa-s), where 1 cP=1 mPa-s. Viscosity may be measured by using for example a viscometer at a given shear rate. Viscosity can also be assessed by positively correlating viscosity with injection force as shown in FIG. 4.

TABLE 1

| Generic name | Viscosity (cP) | | Administration route |
|---|---|---|---|
| | Litterature | Measured | |
| Caprylocaproyl polyoxyl-8 glycerides | 89 | | oral |
| Castor oil, ethoxylated | 722 | | IV |

TABLE 1-continued

| Generic name | Viscosity (cP) | | Administration route |
|---|---|---|---|
| | Litterature | Measured | |
| Corn oil | | 44.9 | IM |
| Cottonseed oil | | 47.7 | IM |
| Glyceryl monooleate | 30-40 | | topical, oral, transdermal |
| Medium chain triglycerides | 30 | 27.12 (20° C.), 22.64 | IV, oral, topical |
| Polyoxyethylene oleictriglycerides | 80 | | |
| Propylene glycol dicaprylocaprate | 12 | 11.16 (20° C.), 9.66 | topical |
| Propylene glycol monocaprylate | 20 | 14.49 (20° C.), 12.05 | |
| Propylene glycol monolaurate | 25 | 26.80 (20° C.), 21.91 | transdermal |
| Sesame oil | | 51.3 | IM, SC, oral |
| Simethicone | 400 | 482.63 (20° C.), 448.37 | IM, IV |
| Thin vegetable oil | 25.4 | 22.7 | oral, topical |

"Shear rate" as used herein means the speed with which a material is deformed. For classical Newtonian fluids, viscosity is not dependent on shear rate. For non-Newtonian fluids, viscosity either decreases or increases with increasing shear rate, e.g. the fluids are "shear thinning" or "shear thickening", respectively.

"Injection force" as used herein means the force measured in Newtons (N) required to push the vehicle or formulation through a 1 mL rigid needle shield glass syringe having a 0.25 inch inside diameter, equipped with a 0.5 inch 26½-gauge needle at a 250 mm/min injection speed using a Zwick/Roell (model 2005) testing instrument (Zwick Roell, Kennesaw, Ga.). An exemplary syringe is a BD (Becton, Dickinson and Company, N.J.) syringe (BD Hypak SCF™ 1 mL Rigid Needle Shield Glass Prefillable Syringe equipped with a 0.5 inch 26½-gauge needle (Product Designator PIRG-001 SCF1MLL 26GA1/2 RNSFM27 EB LTP. 8268589).

"Injectability" as used herein refers to the injection performance of the non-aqueous high concentration suspension formulation through a syringe equipped with a gauge needle during injection. Injectability includes factors such as pressure or force required for injection, evenness of flow, aspiration qualities, and freedom from clogging. Injectability of the formulations of the invention is assessed by comparing the injection force of a formulation that contains a viscosity reducing agent to the same formulation but lacking the viscosity reducing agent. The reduction in the injection force of the formulation containing the viscosity reducing agent reflects improved injectability of that formulation. The viscosity reducing agent containing formulation has improved injectability when the injection force is reduced by at least 10%, for example 10%, 15%, 20%, 25%, 30%, 35%, 40%, 45%, 50%, 55%, 60%, 65%, 70%, 75%, 80%, 85%, 90%, 95%, or 99% when compared to the same formulation but lacking the viscosity reducing agent.

"A viscosity reducing agent" as used herein refers to an agent that, when present in a vehicle or formulation, reduces the viscosity or injection force of the vehicle or formulation compared to the viscosity or injection force of a vehicle or formulation lacking the viscosity reducing agent. The amount of viscosity reducing agent present in the reduced viscosity vehicles or formulations of the invention can range from about 0.2% to 99.9% per volume of the viscosity reducing agent in the hydrophobic agent, for example 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some instances, vehicle may consist of 100% of a viscosity reducing agent. The viscosity reducing agent can reduce the viscosity or injection force of a vehicle or a formulation by at least 10%, for example 10%, 15%, 20%, 25%, 30%, 35%, 40%, 45%, 50%, 55%, 60%, 65%, 70%, 75%, 80%, 85%, or 90%. Exemplary viscosity reducing agents are diethyl sebacate, diethylene glycol monoethyl ether, ethyl alcohol, ethyl oleate (EO), isopropyl alcohol (IPA), isopropyl myristate, linoleic acid, propionic acid, triethyl citrate, propylene glycol, ethanol, propanol, isopropanol, polyethylene glycol, polyperfluoroethers, fluorocarbon (halothane, methoxyflurane, enflurane, isoflurane, sevoflurane and desflurane, etc.), fluorinated ketone, perfluorodecalin, perfluoroacrylate, perfluoromethacrylate, benzyl alcohol, lauryl alcohol, perfluorodecalin, N-Methyl-2-pyrrolidone, glycofurol, polyethylene glygol (PEG), alkyl ketone, lower alkyl ester of citric acid, benzyl benzoate, methyl benzoate, ethyl benzoate, n-propyl benzoate, isopropyl benzoate, butyl benzoate, isobutyl benzoate, sec-butyl benzoate, tert-butyl benzoate, and isoamyl benzoate. Characteristics of exemplary viscosity reducing agents are shown in Table 2.

When the addition of the viscosity reducing agent results in lowering the viscosity or injection force of the vehicle compared to a corresponding vehicle that does not contain the viscosity reducing agent, the vehicle containing the viscosity reducing agent is a "reduced viscosity vehicle". The formulation comprising a reduced viscosity vehicle is "a reduced viscosity formulation". Regardless of the method used to determine and measure viscosity or injection force, the percent reduction in viscosity or injection force in the reduced viscosity vehicle or formulation when compared to the same vehicle or formulation without the viscosity reducing agent will remain approximately the same at a given shear rate.

The term "chemical stability" means that an acceptable percentage of degradation products produced by chemical pathways such as oxidation, deamidation, or hydrolysis are formed. A formulation is considered chemically stable if no more than 5% breakdown products are formed after 18 months at 4° C.

The term "physical stability" means that an acceptable percentage of aggregates (e.g., dimers, trimers or other multimeric aggregates) are formed by the bioactive agent. A formulation is considered physically stable if no more than about 5% aggregates are formed after 18 months at 4° C.

The term "stable formulation" or "stable" as used herein means that at least about 95%, 96%, 97%, 98%, 99%, or 100% physically stable bioactive molecule remains in a formulation after 18 months of storage at +4° C. or equivalent conditions at an elevated temperature, such as a 1 month storage at +40° C. An exemplary stable formulation is a 30% anti-TNFα mAb EO/SO/50/50 formulation that retains at least 98% of the antibody in a monomer form after one month of storage at +40° C.

TABLE 2

| Generic name | Viscosity (cP) | | Administration route |
|---|---|---|---|
| | Litterature | Measured | |
| Diethyl sebacate | 3.9 | 5.59 | topical |
| Diethylene glycol monoethyl ether | 20 | 4.89 | IV, topical, transdermal |
| Ethyl alcohol (EtOH) | 1.2 | 1.48 | IV, IM, SC |
| Ethyl Oleate (EO) | 5.9 | 5.96 | transdermal, IM |
| Isopropyl alcohol (IPA) | 2.43 | 2.35 | IV, oral, transdermal |
| Isopropyl myristate | 7 | 5.1 | topical |
| Linoleic acid | | 18.67 | |

TABLE 2-continued

| Generic name | Viscosity (cP) Litterature | Measured | Administration route |
|---|---|---|---|
| Propionic acid | 1 | 1.65 | |
| Triethyl citrate | | 25.65 | oral |

The term "bioactive molecule" includes proteins, antibodies, peptides, nucleotides, and the like. Synthetically produced, naturally derived or recombinantly produced moieties are included in this term. Bioactive molecules may be analogs, derivatives, agonists, antagonists, or pharmaceutically acceptable salts of bioactive molecules.

The term "protein" means a molecule that comprises at least two amino acid residues linked by a peptide bond to form a polypeptide. Small proteins of less than 50 amino acids may be referred to as "peptides". Proteins may also be referred as "polypeptides".

The term "antibody" includes whole antibodies and any fragments thereof. Antibody fragments comprise at least a portion of an immunoglobulin molecule, such as a complementarity determining region (CDR), a variable region (V), a constant (C) region, or a framework region (FR) from either antibody heavy or light chain. Immunoglobulins can be assigned to five major classes, namely IgA, IgD, IgE, IgG and IgM, depending on the heavy chain C domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

An antibody may be a Fab, F(ab'), F(ab')$_2$, scFv, dsFv, or diabody. An antibody may be a monoclonal antibody (mAb), chimeric, humanized, or human antibody, dimeric, tetrameric or multimeric. Structures of the above mentioned antibody fragments, and techniques for the preparation and use of the antibodies and fragments thereof are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, NY, 1997-2001; Kohler et al., Nature, 256:495-7, 1975; Queen et al., Proc Natl Acad Sci USA, 86:10029-33, 1989; U.S. Pat. No. 4,816,567).

"High concentration" as used herein means a final concentration of equal to or more than 50 mg/mL of a bioactive molecule in a formulation. The concentration of the bioactive molecule may be between 50-1000 mg/mL, between 50-500 mg/mL, or between 50-250 mg/mL.

"Non-aqueous" as used herein means that the vehicle has low solubility in water of less than 0.1 mg/g at physiological pH (about 7.4) and at about 25° C.

"Suspension formulation" as used herein means that the bioactive molecule is insoluble in the vehicle.

"Particle size" as used herein means the average diameter (D50) of the bioactive molecule particulates in a formulation determined by using well known particle sizing instruments, for example laser diffraction particle size analyzer.

This invention describes non-aqueous high concentration reduced viscosity suspension formulations that can be used for administration of bioactive molecules such as antibodies by parenteral route. High viscosity characteristic to high protein concentration formulations may make it difficult to inject the required dose into a patient from the syringe. The formulations of the invention have improved injectability as measured by the injection force of the formulations, while maintaining high concentration of bioactive molecule that will provide the required dose for achieving acceptable therapeutic efficacy. The formulations of the invention have injection forces equal to or below 45 Newton (N), a maximum force that most health care professionals and patients without hand impairment are capable of exerting on a syringe using manual injection. The acceptable injection force level is dependent on the specific drug application and the delivery devices used in the products. Some devices may be able to generate a larger injection force than others.

The concentration of the bioactive molecule in the formulations is shown as % weight (% w/w) and the amount of viscosity reducing agent in a vehicle is shown as % volume (% v/v) unless specifically indicated otherwise. The vehicle compositions are indicated as % volume ratios (% v/v) of the viscosity reducing agent and a hydrophobic agent. For example, an EO/SO/50/50 is a vehicle having 50% ethyl oleate (EO) and 50% sesame oil (SO) by volume.

One embodiment of the invention is a non-aqueous high concentration suspension formulation, comprising:
 a. a vehicle, comprising a hydrophobic agent and a viscosity-reducing agent; and
 b. a bioactive molecule.

The vehicle can be made by combining a hydrophobic agent and a viscosity-reducing agent in liquid forms, and the mixture is heated to form a single-phase material. Standard methods such as differential scanning calorimetry may be used to verify that the components included in the vehicle have been combined such that a single-phase material is formed. Exemplary hydrophobic and viscosity reducing agents are described above. Exemplary vehicles based on sesame oil are shown in Table 4. Sesame oil can be replaced with other exemplary hydrophobic agents as long as the viscosity reducing agent is miscible with the chosen hydrophobic agent.

Any suitable particle formation method may be used to provide the particulate bioactive molecule included in the formulations of the invention. Exemplary well known methods include spray drying, spray-freeze-drying, lyophilization, dessication, granulation, grinding, milling, precipitation, supercritical fluid technology or homogenization processes. The particles prepared by these methods can be further ground in a Waring blender and passed through a series of sieves with determined mesh sizes. The size of the resulting particles of bioactive molecules can be for example between 0.2-250 μm, 0.2-100 μm, 0.2-50 μm, 0.2-20 μm, or 2-13 μm. The particle size may be expressed as an average diameter (D50) of the bioactive molecule particulates in a formulation determined by using well known particle sizing instruments, for example the laser diffraction particle size analyzer (Malvern Mastersizer 2000, Malvern), or as a diameter of the sieve mesh through which the particles do not pass through.

The bioactive molecule may be provided in pure form or may be formulated with excipients that do not interfere with the therapeutic efficacy of the bioactive molecule. For example, it may be desirable to use excipients to mitigate aggregation and oxidation of the bioactive molecule in the non-aqueous formulations, to enhance transition of the bioactive molecule from the non-aqueous vehicle into an environment of use, or to improve formability of the bioactive molecule into particles. Such excipients are for example carbohydrates, nonionic surfactants, buffers, salts, antioxidants and/or amino acids, preservatives and the like.

The bioactive molecule can be formulated for example with a carbohydrate, a nonionic surfactant, and a buffer as excipients. Exemplary carbohydrates are sucrose, trehalose, mannitol, dextran and sorbitol. Exemplary nonionic surfactants are polysorbate 20 (PS-20), polysorbate 80 (PS-80), Triton X-100, Brij-35, Brij-30 and Pluronic F127. The bioactive molecule can be formulated in a buffer having a desirable pH before protein particles are made in order to prevent oxidation, deamidation, hydrolysis, denaturation or aggregation and maintain biological activity of the bioactive molecule during formulation process and storage. Exemplary buffers are acetate, citrate, formate, histidine, succinate, phosphate, carbonate, malate, HEPPSO, HEPES, borate, glycine, aspartic acid, proline, and Tris buffers.

Additional excipients in a formulation may include an amino acid. Exemplary amino acids are histidine, isoleucine, methionine, glycine, arginine, lysine, L-leucine, Tri-leucine, alanine, glutamic acid, L-threonine, and 2-phenylamine.

Additional excipients may include salts. Exemplary salts are sodium chloride, calcium chloride and magnesium chloride.

Additional excipients may include polymers. Exemplary polymers are polyvinylpyrrolidone (PVP), dextran and polyethylene glycols.

The amounts of excipients in the formulation can be determined experimentally based on the activities of the excipients and the desired characteristics of the formulation, such as stability, minimal oxidation, and formability of particles during spray drying.

The bioactive molecule and the excipient may be dissolved into a solution, which is for example lyophilized, spray-dried or spray-freeze-dried to produce particles of the bioactive molecule.

An exemplary bioactive molecule is an antibody or antibody fragment thereof. An exemplary antibody is an anti-tumor necrosis factor-α (TNFα) antibody such as TNV14, TNV15, TNV148, TNV148B and TNV196 shown in FIG. 12 comprising heavy chain variable region sequences shown in SEQ ID NOs: 1 (TNV14), 2 (TNV15), 3 (TNV148), 4 (TNV148B) and 5 (TNV196), and light chain variable region sequences shown in SEQ ID NOs: 6 (TNV14 and TNV15), and 7 (TNV148, TNV148B and TNV196). TNV148B is also named CNTO148. Another exemplary anti-TNFα antibody is HUMIRA® brand of anti-human TNFα antibody (adalimumab), described in U.S. Pat. No. 6,258,652; CAS Registry number 331731-18-1). Anti-TNFα antibody variable regions may be coupled to any constant region, for example a constant region of IgG1 and κ type, respectively. An exemplary IgG1 constant region is shown in SEQ ID NO: 8 and an exemplary κ constant region in SEQ ID NO: 9.

Exemplary formulations of bioactive molecules, for example anti-tumor necrosis factor-α (TNFα) antibodies, can include one or more of following excipients: carbohydrate at about carbohydrate:protein ratio between 0-3, 0.5-3, 1-3, or 1-2; amino acid at about amino acid:protein ratio between 0-2 or 0.3-1.8; amino acid at about ratio wherein the ratio of combined weight of carbohydrate and amino acid to protein is about 0-3, 0.5-3, 1-3, or 1-2; about 0-40 mM, 5-40 mM, 5-20 mM or 5-10 mM histidine buffer; about 0-20 mM, 5-20 mM or 5-10 mM citrate buffer; where excipient:protein ratios are indicated as a w/w ratio, and about 0-0.1% (% w/v), 0.01-0.1% (% w/v) or 0.01-0.05% PS-80 (% w/v). pH may be adjusted at about 5.5. Exemplary anti-TNFα antibody formulations are CNTO148 spray-dried formulations containing 32.5 mg/ml CNTO148, 10 mM histidine, 55 mg/ml sucrose, 10 mg/ml isoleucine, 0.01% PS-80, pH5.5; 32.5 mg/ml CNTO148, 10 mM histidine, 65 mg/ml sucrose, 0.01% PS-80, pH5.5; 32.5 mg/ml CNTO148, 5 mM histidine/5 mM citrate, 65 mg/ml sucrose, 0.01% PS-80, pH5.5; 32.5 mg/ml CNTO148, 10 mM histidine, 5 mg/ml sucrose, 22.5 mg/mL mannitol, 0.01% PS-80, pH5.5; or 32.5 mg/ml CNTO148, 10 mM histidine, 55 mg/ml trehalose, 10 mg/ml isoleucine, 0.01% PS-80, pH5.5; or 65 mg/ml CNTO148, 10 mM histidine, 55 mg/ml sucrose, 0.01% PS-80, pH5.5. PS-80 concentration is indicated as % w/v throughout the application. Spray drying techniques are known to those skilled in the art. An exemplary technique is described in Example 2 below.

To create a suspension formulation of a bioactive molecule, dry particulate material of a bioactive molecule in a solid state (for example powder, crystalline, or amorphous state) with or without excipients is dispersed by stirring within a vehicle. The amount of particulate bioactive molecule included in the formulation may vary depending on for example potency of the bioactive molecule and the route of administration. For example, the bioactive molecule may account for between about 0.1% to 70% (% w/w) of a formulation, with the vehicle accounting for between about 30% and 99.9% (% w/w). The bioactive molecule may be in suspension in a vehicle at a concentration between about 50 mg/mL-1000 mg/mL, 50 mg/mL-500 mg/mL, or 50 mg/mL-250 mg/mL. Exemplary formulation consists of 40% (% w/w) anti-TNFα mAb particles made by spray drying 65 mg/mL anti-TNFα mAb, 55 mg/mL sucrose, 10 mM L-histidine, 0.01% PS-80, pH 5.5 solution and 60% (% w/w) vehicle having sesame oil and ethyl oleate (50:50 ratio by volume). Since the bioactive molecule is present at such a high concentration, the non-aqueous suspension formulation may be used to deliver a bioactive molecule that has a low potency. Since the bioactive molecule is kept in its solid form, long shelf life stability is expected.

Although the embodiments illustrated in the Examples comprise CNTO148 formulations, other antibodies and other anti-TNFα antibodies may be substituted for CNTO148 to develop formulations with similar characteristics to the exemplified CNTO148 formulation, e.g., non-aqueous high concentration reduced viscosity suspension formulations with high stability and good injectability retaining similar bioactivity to aqueous formulations.

Viscosity of the vehicles and the formulations of the invention can be measured using well known rheological instruments, such as a rheometer. Viscosity of a vehicle or a formulation can be measured as a function of shear rate between for example 200-500 $s^{-1}$ at 25° C. by using a AR2000 Rheometer (TA Instruments), and calculating the average viscosity between the measured shear rates, or as a function of a defined shear rate for example $250s^{-1}$. Viscosity of the vehicles and formulations of the inventions can also be assessed by measuring their injection force, which positively correlates with viscosity (FIG. 4). Injection force can be measured by for example loading prepared formulations into a 1 mL rigid needle shield glass syringe having a 0.25 inch inside diameter, equipped with a 0.5 inch 26½ gauge needle and setting the injection speed at for example 250 mm/minutes and recording the piston travel force using a Zwick/Roell (Model 2005) testing instrument (Zwick Roell, Kennesaw, Ga.). An exemplary syringe is a BD (Becton, Dickinson and Company, N.J.) syringe (BD Hypak SCF™ 1 mL Rigid Needle Shield Glass Prefillable Syringe equipped with a 0.5 inch 26½ gauge needle (Product Designator PIRG-001 SCF1MLL 26GA1/2 RNSFM27 EB LTP. 8268589). Percent (%) reduction in the viscosity or injection force is measured to assess effect of viscosity reducing agents in the viscosity and injectability of the formulations of the invention. For example, the non-aqueous high concentration protein formulations of the invention may have 81% reduction in viscosity or 76% reduction in injection force when compared to the formulations without the viscosity reducing agent.

Viscosity of the non-aqueous high concentration suspension formulations of the invention can be further lowered and thus injectability of the formulations improved by modifying the shear rate. The formulations of the invention can be analyzed for their Newtonian or non-Newtonian characteristics by analyzing the dependence of viscosity on shear rate. Non-Newtonian characteristics of formulations can depend on protein concentration and amount of viscosity reducing agent in a formulation. Increasing protein concentration in the formulations of the invention can shift the formulation characteristics to non-Newtonian shear thinning, and thus increasing share rate during manufacturing can reduce viscosity and improve processing of these formulations. Increasing the amount of viscosity reducing agent in a formulation may shift the formulation characteristics to Newtonian, in which instance modulation of share rate has little or no effect on viscosity. Preparation of the Formulations of the Invention Include assessing effect of shear rate on viscosity, and adjusting shear rate to for example between 10-1000 l/s or 50-500 l/s to obtain formulations with appropriate viscosity values.

Formulations of bioactive molecules of the present invention demonstrate improved stability over aqueous formulations, and retain at least 95% of the bioactive molecule in a stable form after storage for one month at +40° C. Stability of the formulations can be measured using well known methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein.

Another embodiment of the invention is a non-aqueous high concentration suspension formulation, comprising a vehicle comprising sesame oil and ethyl oleate; and a bioactive molecule.

Another embodiment of the invention is a method of reducing an injection force to about 45 Newton (N) or less of a formulation containing ≥50 mg/ml of a protein in a vehicle comprising a hydrophobic agent, comprising: adding at least 28% by volume of a viscosity reducing agent into the vehicle comprising a hydrophobic agent; or utilizing protein particles having particle size between about 2 µm-13 µm to prepare the formulation, wherein the injection force is measured using a 1 mL rigid needle shield glass syringe having a 0.25 inch inside diameter, equipped with a 0.5 inch 26½ gauge needle at a 250 mm/min. injection speed.

Several parameters can be changed in order to maintain the injection force of the non-aqueous high concentration suspension formulations of the invention at or below 45 Newton (N). These parameters are for example protein concentration, particle size, and amount of viscosity reducing agent in the formulation, and the injection speed used for a selected syringe with a specified needle gauge. The amount of viscosity reducing agent in the formulations having injection force at or below 45 N may be for example between 0.2%-99.9%, the amount of protein may be between 1-40% (% w/w), and the particle size may be about 2 µm-13 µm. Exemplary non-aqueous formulations containing a hydrophobic agent, a viscosity reducing agent and a bioactive molecule, and having injection forces below 45 N are formulations having at least 20% (% w/w) protein concentration with a particle size of about 2 µm-13 µm, and at least 28% of EO in a vehicle; 20% (% w/w) 2 µm BSA particle suspensions in EO/SO/28/72, EO/SO/50/50 or in 100% EO; 20% (% w/w) anti-TNFα mAb suspensions in EO/SO/50/50, EO/SO/73/30, EO/SO/85/15, or in 100% EO; 30% and 40% (% w/w) anti-TNFα mAb suspensions in EO/SO/50/50; 40% 13 µm BSA particle suspensions in EO/SO/50/50; 50% (% w/w) 2 µm BSA particle suspensions in 100% EO with injection speed of 50 mm/min; and 50% (% w/w) 13 µm BSA particle suspensions with injection speed between 50-250 mm/min.

Another embodiment of the invention is a method of making a non-aqueous high concentration suspension formulation of a bioactive molecule, comprising providing a bioactive molecule; providing a hydrophobic agent; providing a viscosity reducing agent; mixing the hydrophobic agent and the viscosity reducing agent to form a vehicle; and adding the bioactive molecule into the vehicle formed in step d. at a concentration of equal to or more than 50 mg/mL.

The formulations of the invention may be preloaded in a syringe or any suitable small-volume container using well known methods and, therefore, are injection ready without mixing, reconstitution, or any additional preparations. The formulations of the invention in the preloaded syringe may be injected by hand or alternatively using an autoinjector such as an automatic injection pen, an auto-injector, various automatic injection pumps including patch pump, and needle free injection devices. The formulations of the invention can be introduced into a host by parenteral routes, such as by subcutaneous (SC) or intramuscular (IM) injection. The formulations can be administered through needles about one-half to two inches long, between 20-31 gauge, with an internal diameter in the range of 133 to 604 microns. The injection-ready non-aqueous high concentration suspension formulation of the invention can have favorable local tolerance (or biocompatibility), low injection force, and formulation flexibility. The high concentration of the bioactive molecule in the injection-ready non-aqueous suspension formulation can be achieved independent of the molecular structure and molecular weight of the bioactive molecule.

The present invention will now be described with reference to the following specific, non-limiting examples.

Example 1

Screening of Viscosity Reducing Agents for Non-Aqueous Vehicles

Viscosity reducing agents were added to sesame oil in a concentration of 0.2%-50% by volume. All viscosity reducing agents were of GRAS (Generally Recognized As Safe) material. The mixture was placed in a closed 20 mL scintillation vial and vortexed for 30 seconds, and visually inspected for any immiscibility. Some of the viscosity reducing agents were found not to be miscible with sesame oil and were not screened further. Table 3 shows miscibility of exemplary viscosity reducing agents with sesame oil. Y and N denote that the tested viscosity reducing agent was miscible or was not miscible, respectively, with sesame oil at the concentration tested.

TABLE 3

| Viscosity reducing agent | Viscosity reducing agent % (v/v) | | | | | | | | |
|---|---|---|---|---|---|---|---|---|---|
| | 0.2 | 0.7 | 1.7 | 3.1 | 5.4 | 9.7 | 17.2 | 30.0 | 50.0 |
| Diacetyl | Y | Y | Y | Y | Y | Y | Y | N | N |
| Ethanol | Y | Y | Y | Y | Y | Y | N | N | N |
| Ethyl oleate | Y | Y | Y | Y | Y | Y | Y | Y | Y |
| Isopropanol | Y | Y | Y | Y | Y | Y | Y | Y | N/A |
| Lactic acid | N | N | N | N | N | N | N | N | N |
| Linoleic acid | Y | Y | Y | Y | Y | Y | Y | Y | N/A |
| Propionic acid | Y | Y | Y | Y | Y | Y | Y | Y | N/A |
| Propylene glycol | N | N | N | N | N | N | N | N | N |
| Triethyl citrate | Y | Y | Y | Y | Y | Y | N | N | N |

Some viscosity reducing agents such as ethyl oleate, isopropanol, linoleic acid, and propionic acid were miscible with sesame oil over the range of tested concentrations, while propylene glycol was not miscible at all. Some agents were miscible with sesame oil only at certain ratios of viscosity reducing agent and sesame oil.

For the measurement of vehicle viscosity, once the homogeneous solution was formed, 290 µL of each vehicle to be tested were pipetted onto the AR2000 Rheometer (TA Instruments)

TABLE 4

| Viscosity reducing agent | Viscosity reducing agent (% v/v) | Sesame oil (% v/v) | Mean Viscosity (cP) | SD* | Viscosity decrease (cP)** |
|---|---|---|---|---|---|
| Ethyl oleate | 0 | 100 | 51.25 | 0.32 | |
| | 0.2 | 99.8 | 50.14 | 0.06 | −1.11 |
| | 0.7 | 99.3 | 50.09 | 0.22 | −1.16 |
| | 1.5 | 98.5 | 48.15 | 0.1 | −3.1 |
| | 3 | 97 | 45.85 | 0.81 | −5.4 |
| | 5.5 | 94.5 | 43.01 | 0.05 | −8.24 |
| | 9.5 | 90.5 | 38.8 | 0.36 | −12.45 |
| | 17 | 83 | 32.65 | 0.15 | −18.6 |
| | 28 | 72 | 25.64 | 0.14 | −25.61 |
| | 50 | 50 | 16.7 | 0.09 | −34.55 |
| | 75 | 25 | | | |
| | 85 | 15 | | | |
| | 100 | 0 | 5.96 | 0.19 | −45.29 |
| Linoleic acid | 3 | 97 | 50.21 | 1.26 | −1.04 |
| | 9.5 | 90.5 | 46.98 | 0.38 | −4.27 |
| | 17 | 83 | 42.3 | 0.74 | −8.95 |
| | 28 | 72 | 38 | 0.33 | −13.25 |
| Propionic acid | 3 | 97 | 42.48 | 0.91 | −8.77 |
| | 9.5 | 90.5 | 30.99 | 0.49 | −20.26 |
| | 17 | 83 | 21.06 | 0.14 | −30.19 |
| | 28 | 72 | 12.83 | 0.22 | −38.42 |
| Diethyl sebacate | 3 | 97 | 46.33 | 0.8 | −4.92 |
| | 9.5 | 90.5 | 38.82 | 0.2 | −12.43 |
| | 17 | 83 | 30.85 | 0.42 | −20.4 |
| | 28 | 72 | 23.59 | 0.23 | −27.66 |
| Isopropyl myristate | 3 | 97 | 45.92 | 1.3 | −5.33 |
| | 9.5 | 90.5 | 38.55 | 0.53 | −12.7 |
| | 17 | 83 | 31.88 | 0.2 | −19.37 |
| | 28 | 72 | 24.09 | 0.18 | −27.16 |
| Isopropyl alcohol (IPA) | 3 | 97 | 43.95 | 0.73 | −7.3 |
| | 9.5 | 90.5 | 33.14 | 0.13 | −18.11 |
| | 17 | 83 | 25 | 0.4 | −26.25 |
| | 28 | 72 | 13.81 | 0.05 | −37.44 |
| Ethanol (EtOH) | 3 | 97 | 41.96 | 0.42 | −9.29 |
| | 9.5 | 90.5 | 31.25 | 1.58 | −20 |
| Triethyl citrate | 3 | 97 | 49.76 | 0.09 | −1.49 |
| | 9.5 | 90.5 | 45.36 | 0.74 | −5.89 |

*standard deviation
**comparison to SO vehicle equipped with a 40 mm, 1° acrylic cone geometry. The shear stress was recorded as a function of shear rate up to 500 s$^{-1}$ at 25° C. The viscosity was automatically calculated by the software, and the average of the viscosity between 200 and 500 s$^{-1}$ was reported.

Each sample was analyzed in triplicates. Sesame oil without the viscosity reducing agent was used as a control. Table 4 shows the average viscosity values for exemplary vehicles generated.

The decrease in viscosity of the resulting vehicle was proportional to volume or weight fraction of viscosity reducing agents added. Since sesame oil (SO), ethyl oleate (EO), ethanol (EtOH) and isopropyl alcohol (IPA) have been used in marketed parenteral products, they were selected for further testing.

Example 2

Preparation of Non-Aqueous High Concentration Low Viscosity Formulations

Preparation of Particles of Bioactive Molecules

Lyophilization:

Bovine serum albumin (BSA) (Sigma-Aldrich, St. Louis, Mo., USA) and human anti-TNFα monoclonal antibody (mAb) were dissolved in 6.5 mM sodium phosphate buffer, pH 6.0, at a protein concentration of 65 mg/mL. Pharmaceutically acceptable excipients such as sucrose and Tween 80 (or polysorbate 80, PS-80) were optionally added to the protein solution with the concentration of sucrose and Tween 80 in the final solution of 0-9.0% and 0-0.01% (% w/v), respectively. The protein solution was lyophilized using standard protocols.

The lyophilized protein or mAb powder was further ground in a Waring blender and passed through a series of sieves with determined mesh sizes. The grinding/seizing process produced protein or mAb particles with the particle size of 0.2-250 µm.

Spray Drying:

Particles of bovine serum albumin (BSA) (Sigma-Aldrich, St. Louis, Mo., USA) and human anti-TNFα monoclonal antibodies were prepared using a spray drying process. The formulations (Table 5) were spray-dried using a Yamato Mini Spray dryer at the following process parameters: atomizing air: 2 psi, inlet temperature: 120° C., aspirator dial: 7.5, solution pump: 2-4, main air valve: 40-45 psi. The average diameter, (D50) of the spray dried bioactive molecule particulates was measured by a laser diffraction particle size analyzer (Malvern Mastersizer 2000, Malvern), and particles with a size range of 1~20 µm were obtained. Exemplary preparations are shown in Table 5.

TABLE 5

| Bioactive molecule | Bioactive molecule (mg/mL) | Sucrose (% w/v) | TWEEN ® 80 (% w/v) |
|---|---|---|---|
| BSA | 65 | 5.5 | 0.0065 |
| BSA | 65 | 3 | 0.0065 |
| BSA | 100 | 4.5 | 0.0065 |
| anti-TNFα mAb | 100 | 8.5 | 0.0065 |

Preparation of Non-Aqueous Vehicles

Sesame oil was cleaned with aluminum oxide powder to reduce the peroxide level, and was then filtered through sterile, 0.2 µm PTFE filters. Viscosity reducing agents were added to sesame oil in a concentration of 0.2-85% by volume (% v/v), or in some instances were used without sesame oil. For some formulations, ethanol was added in the vehicle at about 0.2-10% by volume. The mixture was placed in a closed container and mixed for 1 hour at room temperature to form a homogeneous solution. Table 4 shows the non-aqueous vehicles prepared.

Preparation of Formulations

The non-aqueous vehicles prepared were mixed with particles of bioactive molecules prepared by lyophilization or spray drying. A stirrer with a stainless steel spatula blade was used to blend the particles into the vehicle at 50-1000 rpm for 5~30 minutes at room temperature. The particle loading was about 1-50% by weight leading to the protein concentration in the final formulation about 10-500 mg/mL. After a homogeneous suspension was formed, the formulations were filled into a glass injection syringe. The formulations were stored at refrigerated temperature (4° C.) prior to injection. Table 6 shows the prepared formulations.

Example 3

Stability of Lyophilized Bioactive Molecules in Non-Aqueous Vehicles

Ethyl oleate (EO) or medium chain triglyceride (MCT; LABRAFAC™ Lipophile WL 1349, Gattefossé, France) was added to sesame oil (SO) in a concentration of 2-50% by volume. The mixture was placed in a closed 20 mL scintillation vial and vortexed for 30 minutes. After a complete mixing, lyophilized anti-TNFα antibody powders were weighed into a 3 mL vacutainer tube, and an adequate amount of vehicle was added to the tube to a final protein content of 10 or 20% (% w/w), which corresponded to 53.6 or 107.2 mg/mL anti-TNFα antibody concentration, respectively.

The suspension was made homogeneous by brief vortex; the tubes were then sealed. The suspensions were stored at 37° C. After one and four weeks of storage, the samples were extracted.

TABLE 6

| Vehicle Composition (% v/v) | Vehicle (% w/w) | Protein | Protein concentration (% w/w) | Protein concentration mg/mL* |
|---|---|---|---|---|
| SO (100) | 60 | IL-12p40 mAb | 40 | 216.7 |
| EO (100) | 60 | TNFα mAb | 40 | 214.4 |
| EO (100) | 70 | TNFα mAb | 30 | 160.8 |
| EO (100) | 80 | TNFα mAb | 20 | 107.2 |
| EO (100) | 90 | TNFα mAb | 10 | 53.6 |
| MCT (100) | 80 | TNFα mAb | 20 | 107.2 |
| MCT (100) | 90 | TNFα mAb | 10 | 53.6 |
| SO (100) | 60 | TNFα mAb | 40 | 214.4 |
| SO (100) | 70 | TNFα mAb | 30 | 160.8 |
| SO (100) | 80 | TNFα mAb | 20 | 107.2 |
| SO (100) | 90 | TNFα mAb | 10 | 53.6 |
| SO/EO (50/50) | 60 | TNFα mAb | 40 | 214.4 |
| SO/EO (50/50) | 70 | TNFα mAb | 30 | 160.8 |
| SO/EO (50/50) | 80 | TNFα mAb | 20 | 107.2 |
| SO/EO (50/50) | 90 | TNFα mAb | 10 | 53.6 |
| SO/EO (50/50) | 95 | TNFα mAb | 5 | 26.8 |
| SO/EO (50/50) | 99 | TNFα mAb | 1 | 5.4 |
| SO/EO (72/28) | 80 | TNFα mAb | 20 | 107.2 |
| SO/EO (72/28) | 90 | TNFα mAb | 10 | 53.6 |
| SO/EO (15/85) | 80 | TNFα mAb | 20 | 107.2 |
| SO/EO (25/75) | 80 | TNFα mAb | 20 | 107.2 |
| SO (100) | 50 | BSA | 50 | 500.0 |
| SO (100) | 60 | BSA | 40 | 400.0 |
| SO (100) | 70 | BSA | 30 | 300.0 |
| SO (100) | 80 | BSA | 20 | 200.0 |
| SO (100) | 90 | BSA | 10 | 100.0 |
| SO (100) | 95 | BSA | 5 | 50.0 |
| SO (100) | 99 | BSA | 1 | 10.0 |
| SO/EO (50/50) | 50 | BSA | 50 | 500.0 |
| SO/EO (50/50) | 60 | BSA | 40 | 400.0 |
| SO/EO (50/50) | 70 | BSA | 30 | 300.0 |
| SO/EO (50/50) | 80 | BSA | 20 | 200.0 |
| SO/EO (50/50) | 90 | BSA | 10 | 100.0 |
| SO/EO (50/50) | 95 | BSA | 5 | 50.0 |
| SO/EO (50/50) | 99 | BSA | 1 | 10.0 |
| SO/EO (72/28) | 80 | BSA | 20 | 200.0 |
| EO (100) | 50 | BSA | 50 | 500.0 |
| EO (100) | 60 | BSA | 40 | 400.0 |
| EO (100) | 70 | BSA | 30 | 300.0 |
| EO (100) | 80 | BSA | 20 | 200.0 |
| EO (100) | 90 | BSA | 10 | 100.0 |
| EO (100) | 95 | BSA | 5 | 50.0 |
| EO (100) | 99 | BSA | 1 | 10.0 |
| MCT | 80 | BSA | 20 | 200.0 |

*final concentration in the suspension formulation

Briefly, 1 mL of 1:1 mixture −20° C. pre-chilled acetone/dichloromethane was added to the tube and the content was mixed on a shaker at 4° C. for 20 min. The tube was spun for 4 min at 2900 g, and the supernatant was removed. The extraction process was repeated twice, and the protein pellet was dried for 2 hr using a SpeedVac. The pellet was dissolved in the mobile phase (0.2M phosphate buffer, pH 6.8) to a working concentration of 10 mg/mL. 20 µL of the solution was injected onto an Agilent SEC-HPLC system with a flow rate of 1 mL/min. The native, aggregated, and fragmented forms of anti-TNFα antibodies were separated by a BioSil SEC250 column (BioRad, Hercules, Calif.) and monitored at 214 and 280 nm wavelengths on a size exclusion chromatograph (SEC).

Storage stability of tested suspension formulations containing anti-TNFα antibody particles is shown in FIG. 1, and was measured as a % of monomer content (e.g. native mAb) retained in a sample. As a control, aqueous formulations containing anti-TNFα mAb in PBS pH 7.4 were prepared and analyzed. Each non-aqueous suspension formulation showed higher stability compared to the aqueous formulation and they were comparable to lyophilized protein powder in terms of protein monomer contents at the same stress condition. Addition of viscosity reducing agents ethyl oleate (EO) into sesame oil or replacing sesame oil with medium chain triglyceride (MCT) such as Labrafac™ Lipophile WL 1349 (Gattefossé) had no effect on protein stability within 4 weeks of storage time.

Example 4

Injectability of High Concentration Formulations is Affected by Vehicle Composition, Protein Concentration and Particle Size Measurement of piston travel force (e.g. injection force) was used as an assessment to measure effects of various parameters on the injectability of non-aqueous high concentration suspension formulations of the invention.

Effect of Vehicle Composition

Injectability of 20% (% w/w) BSA and 20% (% w/w) anti-TNFα antibody formulations were assessed by measuring the force required to push the suspension through a gauge needle using a Zwick/Roell (Model 2005) testing instrument. BSA particles were prepared by spray drying 100 mg/mL BSA in water, and anti-TNFαmAb particles were prepared by spray drying 65 mg/mL protein, 55 mg/mL sucrose, 10 mM L-histidine, 0.01% PS-80, pH 5.5. Protein formulations were prepared by mixing protein particles as described above with sesame oil containing increasing amounts by volume of viscosity reducing agent ethyl oleate (0%, 3%, 9.5%, 17%, 20%, 25%, 28%, 30%, 40%, 50%, 75%, 85%, or 100% (% v/v)). Prepared formulations were then loaded into BD (Becton, Dickinson and Company, N.J.) syringes (BD Hypak SCF™ 1 mL Rigid Needle Shield Glass Prefillable Syringe equipped with a 0.5 inch 26 gauge needle (Product Designator PIRG-001 SCF1MLL 26GA1/2 RNSFM27 EB LTP. 8268589). The syringes were filled with approximately 0.5 cc of the formulations, the injection rate was set at approximately 250 mm/minute unless specifically indicated otherwise, and the piston travel force was recorded. The injection testing was conducted at room temperature.

Increasing amount of ethyl oleate (EO) in sesame oil (SO) significantly reduced injection force and thus improved injectability of suspension formulations of both 2 μm and 13 μm size protein particles. The injection force for 20% (w/w) (200 mg/mL) suspension of 2 μm BSA particle in EO/SO/28/72 was 35.3 N, and in EO/SO/50/50 21.5 N, latter being a 67% decrease compared with sesame oil control without viscosity-reducing agent (64.65 N) (FIG. 2A). Using 100% EO vehicle further reduced injection force to 12.1 N. Similar reduction in injection force was demonstrated with anti-TNFα mAb formulations with increasing amount of ethyl oleate in sesame oil. For example, the injection force for 20% (w/w) (108.6 mg/mL) suspension with 3.1 μm anti-TNFα mAb particles in EO/SO/50/50 was reduced to 29.5 N, and in EO/SO/70/30 to 21.1 N from the injection force of 71.3 N for 20% (w/w) anti-TNFα mAb in SO (FIG. 2B). The results demonstrate that addition of viscosity reducing agent in a vehicle significantly improved injectability of non-aqueous high concentration suspension formulations by reducing injection force. A non-aqueous high concentration suspension formulation having injection force equal or less than about 45 N can thus be manufactured by increasing the amount of ethyl oleate in sesame oil vehicle containing formulations to equal to or more than 28% by volume.

Effect of Protein Concentration

Injection force was affected by protein concentration in the non-aqueous suspension formulations. FIG. 3A shows combined effect of increased 8.2 μm anti-TNFα particle antibody concentration (20-40% (% w/w); 108.3-216.7 mg/mL) and increased amount of viscosity reducing agent in the injection force of the formulations. X-axis indicates the concentration of anti-TNFα antibody used in each experiment. Using up to 30% mAb concentration in EO/SO/50/50 resulted in injection force of 42.8 N. The injection force at this antibody concentration could be reduced to 20.5 N by utilizing 100% EO as a vehicle. FIG. 3B shows the effect of increasing concentration of anti-TNFα mAb (0-40% (% w/w; 0216.7 mg/mL) in EO/SO/50/50 formulations in both injection force and viscosity. FIG. 3C shows effect of increasing concentration of BSA (particle size 2 μm, 0-40% (% w/w); 0-400 mg/mL) in 100% SO, EO/SO/50/50 and in 100% EO vehicles. In order to reduce injection force to equal or less than about 45N, the formulations may contain about 20% (% w/w) or less of protein and at least 28% EO in a vehicle, 30% or less of protein and at least 50% EO in a vehicle, or a protein concentration of about 40% or less of protein in 100% EO. The experiments conducted also demonstrated that injection force and viscosity of the non-aqueous high concentration suspension formulations are correlated. FIG. 4*a* demonstrates the correlation in 20% (% w/w) anti-TNFα mAb suspension formulations. FIG. 4*b* demonstrates the correlation in all anti-TNFα mAb suspension formulations tested. Thus, injection force can be used both as a measure of viscosity as well as injectability. Appropriately modifying both protein concentration and amount of viscosity reducing agent in the non-aqueous high concentration suspension formulations positively impact injectability of the formulations.

Effect of Particle Size

Effect of particle size on injectability was assessed by measuring the effect of different particle sizes on injection force of the tested formulations. Formulations containing 2 μm and 13 μm BSA particles over concentration range 1-50% (% w/w) (10-500 mg/mL) were prepared in EO/SO/50/50 vehicle. In these formulations, injection force increased with increasing protein concentration and decreased with increasing particle size (FIG. 5). For example, to achieve an injection force equal to or less than 45 N, a 40% (% w/w) protein formulation with 13 μm particle size in EO/SO/50/50 can be used. Maintaining a constant mass of particles in a suspension while increasing the particle size of the solid phase leads to the reduced number of particles in the system. Therefore the suspensions with increasing particle size had less particle-particle interactions and a decreased resistance to flow, leading to the decreased injection force. The results demonstrate that at higher protein concentration such as at 40% (% w/w) choice of particle size in non-aqueous suspension formulations has a significant effect on injection force and thus injectability of the formulations. For example, formulations with 40% (5 w/w) 13 μm protein particles have injection force of 40.5 N, whereas the same formulations with 2 μm protein particles have injection force of 57 N. Therefore, injectability of suspension formulations of the invention can be improved by optimizing both protein concentration and particle size, as well as amount of viscosity reducing agents in the formulations.

Example 5

Viscosity of Non-Aqueous High Concentration Suspension Formulations can be Reduced by Increasing Shear Rate Effect of both vehicle choice and protein concentration on viscosity with varying share rates was studied. 290 μL of formulations containing 1-40% (% w/w) anti-TNFα antibody in EO/SO/50/50 or in SO were pipetted onto the AR2000 Rheometer (TA Instruments) equipped with a 40 mm, 1° acrylic cone geometry. The viscosity scan for each formulation was measured at 25° C. when shear rate increased from ~8 $s^{-1}$ to 5000 $s^{-1}$.

Depending on a vehicle used, 20% (% w/w) anti-TNFα mAb formulations demonstrated either Newtonian (anti-TNFα mAb in EO/SO/50/50) or non-Newtonian shear thinning (anti-TNFα mAb in SO) behavior (FIG. 6*a*). At 30% (% w/w) or higher protein concentrations, anti-TNFα mAb EO/SO50/50 formulations changed their behavior from Newtonian to non-Newtonian shear thinning (FIG. 6*b*).

Assessing the shear thinning behavior of the formulations of the invention is critical to their downstream processing and manufacturing. The highly concentrated protein formulations often result in increased viscosity that poses a significant challenge during process, manufacture, and storage. As shown in FIGS. 6*a* and 6*b*, evaluating effect of shear rate on viscosity and increasing shear rate appropriately during processing and manufacturing of the formulations in the invention can significantly reduce viscosity and therefore improve processability of the formulations.

Example 6

Adjustment of Injection Speed to Modify Injection Force

Figure 7A:
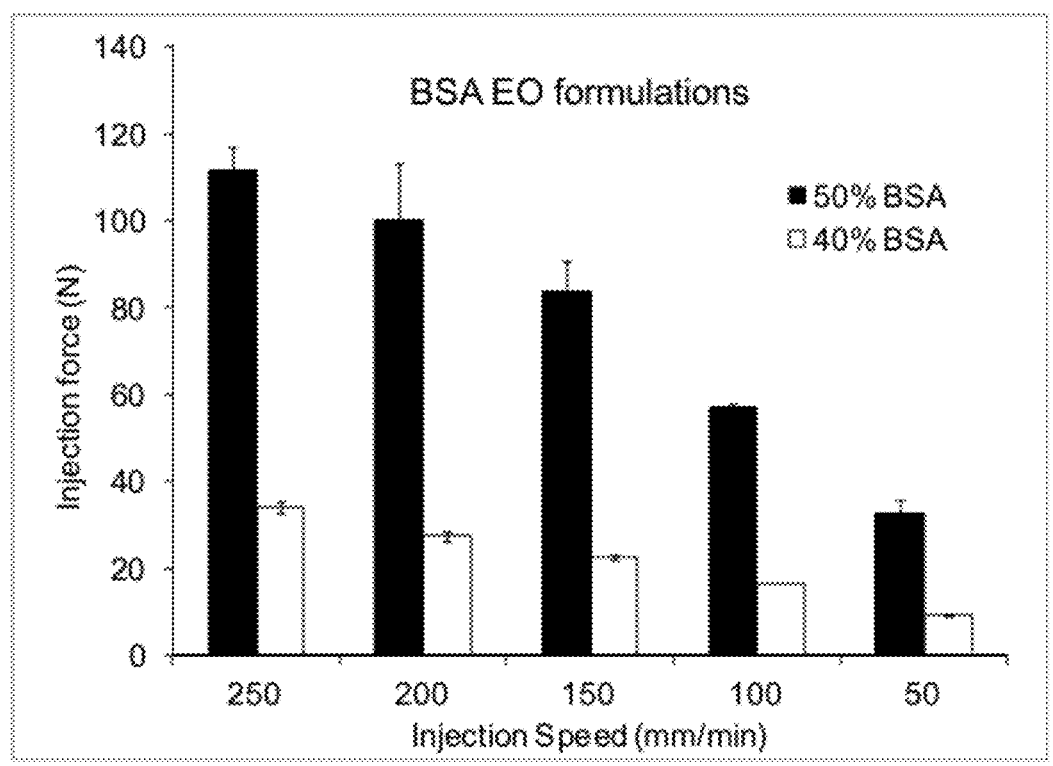
FIG. 7. Effect of injection speed on injection force A. BSA particles at different concentrations in formulations; B. BSA particles of different sizes in EO vehicle; C. anti-TNFα mAb at different concentrations in EO/SO/50/50.
Figure 7B:
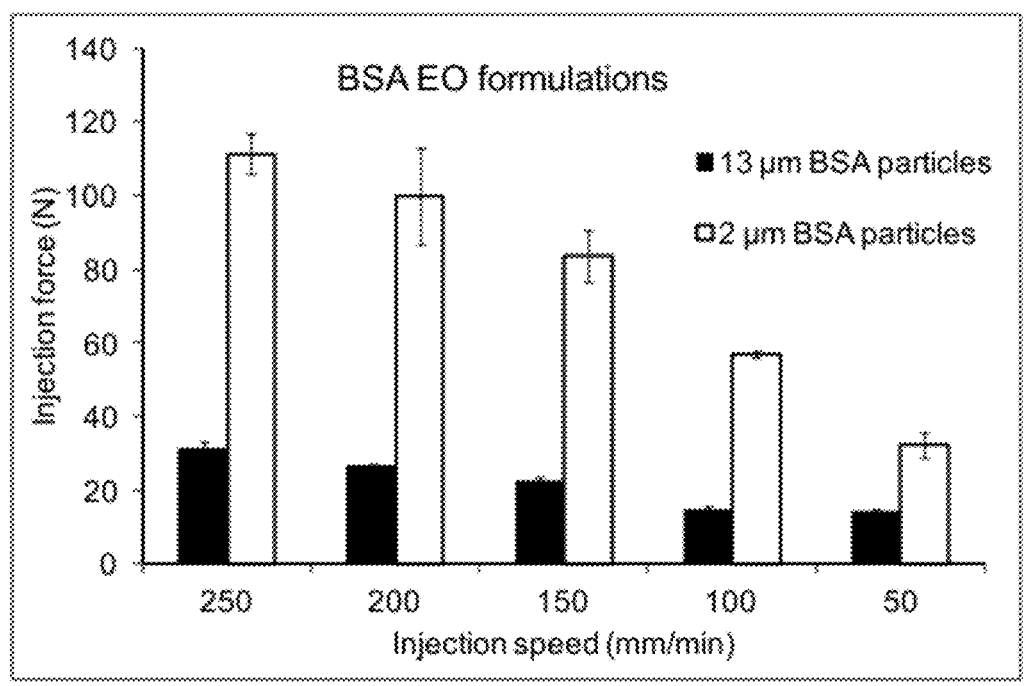
Figure 7C:
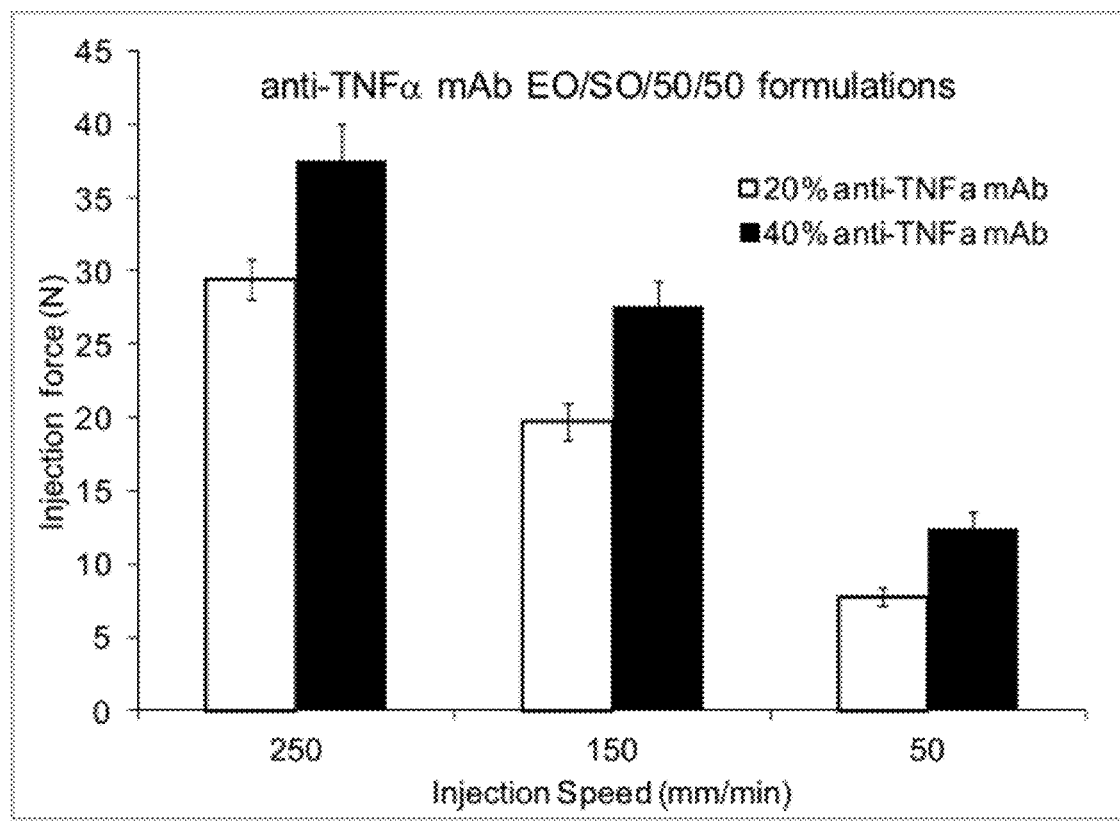
Figure 8A:
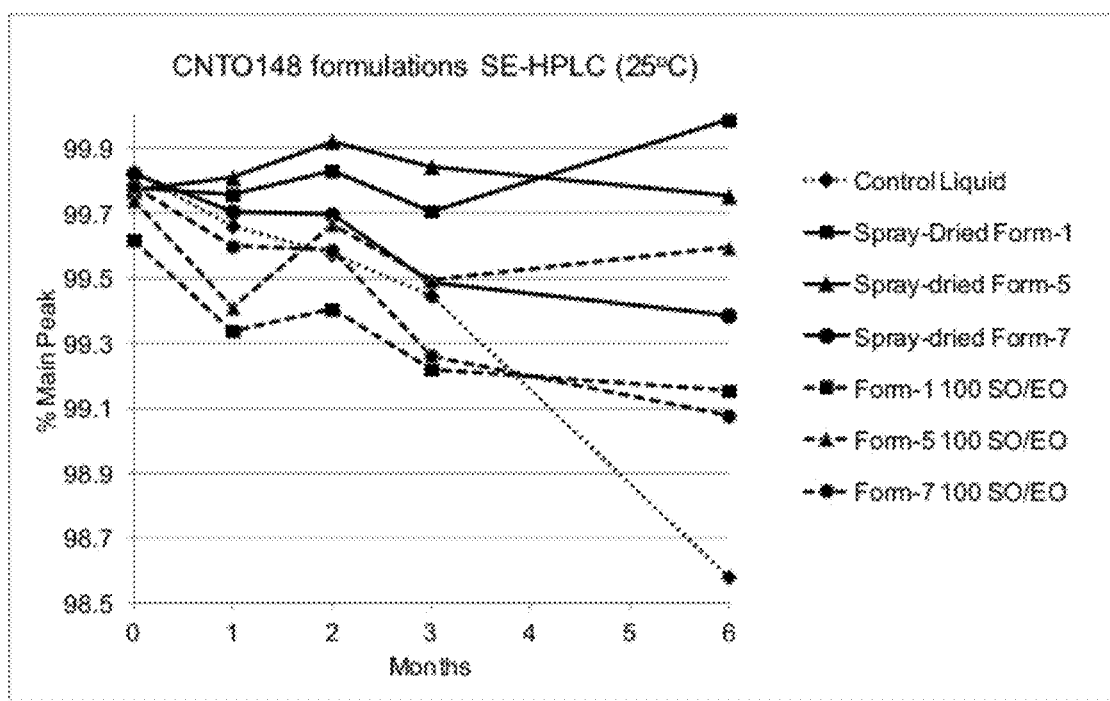
FIG. 8. Stability of CNTO148 A) spray-dried and 100 mg/mL suspension formulations and B) 100 mg/mL and 200 mg/mL suspension formulations at 25° C. measured by SE-HPLC. Nt=suspension not treated with aluminium oxide. Form-1, Form-5 and Form-7 are spray-dried formulations of experiment SD_1 in Table 7. SO/EO=EO/SO/50/50.
Figure 8B:
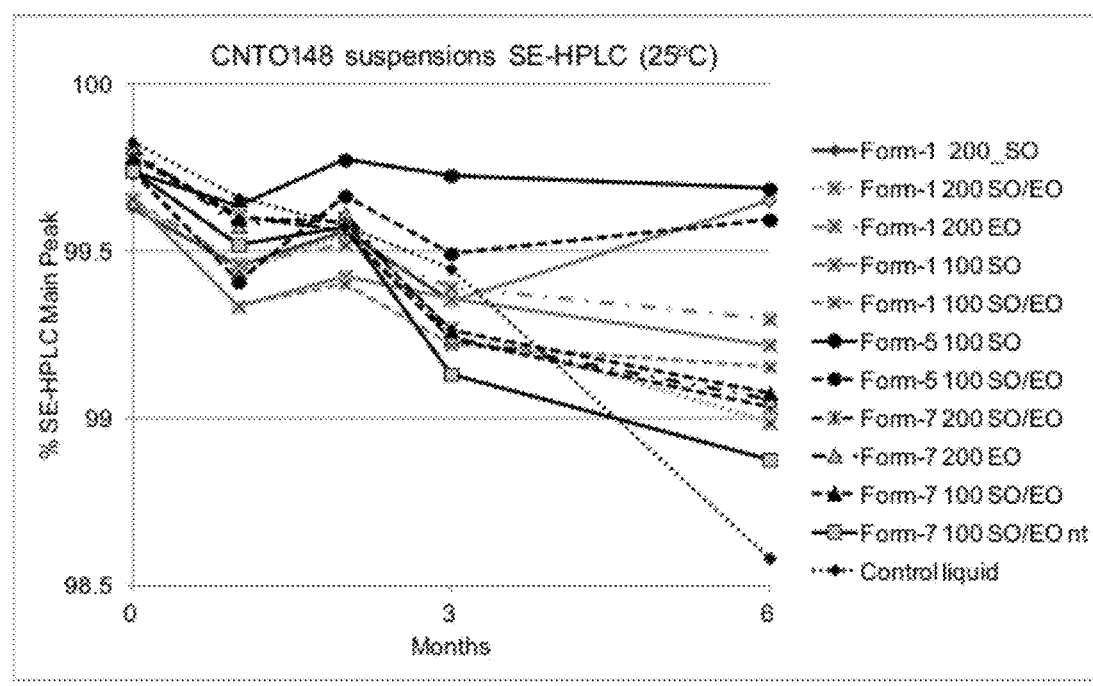
Figure 9A:
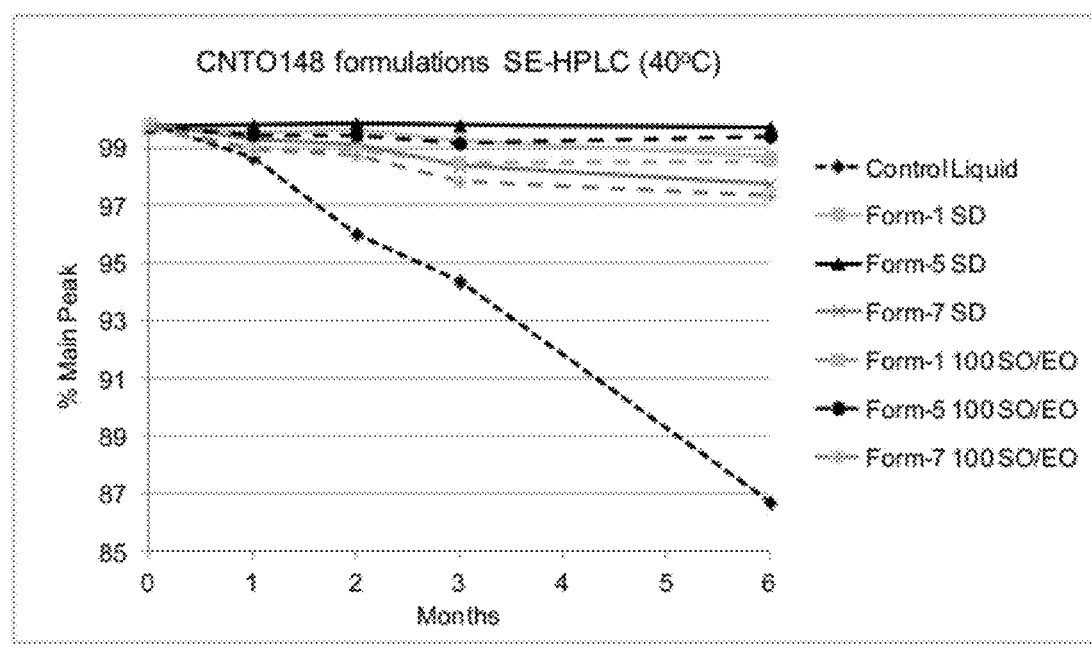
FIG. 9. Stability of CNTO148 A) spray-dried and 100 mg/mL suspension formulations and B) 100 mg/mL and 200 mg/mL suspension formulations at 40° C. measured by SE-HPLC. Nt=suspension not treated with aluminium oxide. Form-1, Form-5 and Form-7 are spray-dried formulations of experiment SD_1 in Table 7. SO/EO=EO/SO/50/50. SD=spray-dried.
Figure 9B:
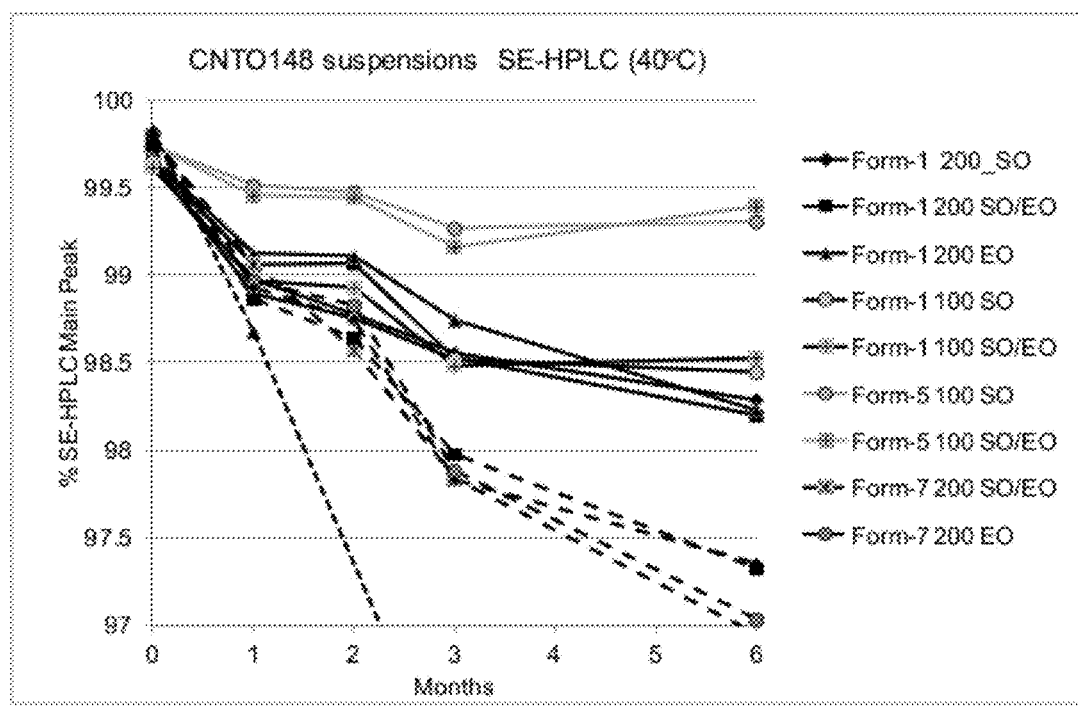
Figure 16:
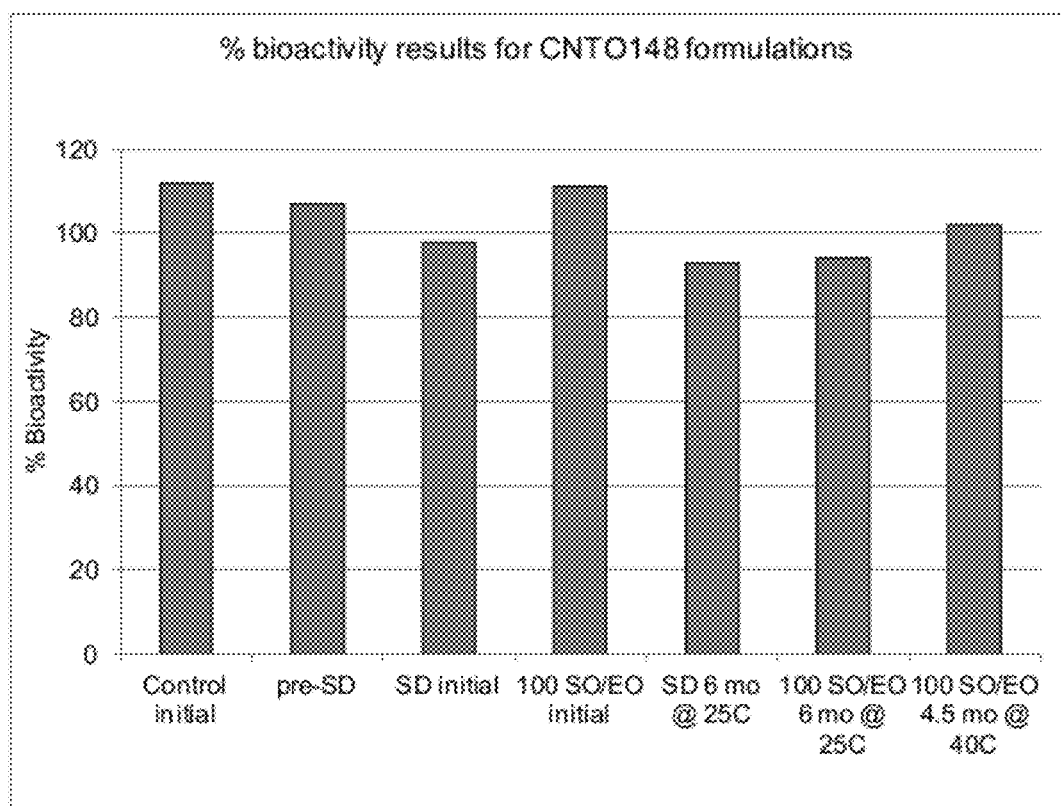

Injection force was assessed for 40-50% (% w/w) (400-500 mg/mL) 2 μm and 13 μm BSA particles in EO (FIG. 7A, 7B) and for 20-40% (% w/w) (108.33-216.67 mg/mL) anti-TNFα antibody in EO/SO/50/50 (FIG. 7C) using various injection speeds. Injection speed affected injection force in a protein concentration-dependent manner. At 40% (% w/w) BSA, injection force was less dependent on injection speed. However, at 50% (% w/w) BSA concentration, decreasing injection speed from 250 mm/min. to 50 mm/min. significantly reduced injection force from 111.4 N to 32.4 N (FIG. 7A). Effect on injection force by injection speed was also affected by particle size. Injection force of formulations with larger particle sizes was less affected by injection speed, whereas injection force of formulations with smaller particle sizes was significantly affected by injection speed (FIG. 7B). Utilizing 13 μm BSA particles with injection speeds between 50-250 mm/min. resulted in injection speeds equal to or less than 45 N. Injection speed also affected the injection force of the anti-TNFα antibody formulations, reduced injection speeds reducing injection force (FIG. 7C).

Example 7

Optimization of Dry Particle Formulations

Formulations of anti-TNFα antibody CNTO148 such as those shown in Table 7 were prepared by spray-drying or lyophilization as described in Example 2. Formulations for spray drying or lyophilization of CNTO148 can include one or more of following excipients: sucrose at about sucrose:protein ratio between 0-3, sucrose+amino acid at (sucrose+amino acid):protein ratio between 0-3, about 0-40 mM histidine buffer, about 0-10 mM citrate buffer, trehalose at about trehalose:protein ratio between 0-1.8, mannitol at about mannitol:protein ratio between 0-1.8, sorbitol at about sorbitol: protein ratio between 0-1.8, amino acid at about (amino acid): protein ratio between 0-1.8; ratios above indicated as w/w ratio, and about 0.01-0.1% PS-80 (% w/v). pH may be adjusted at about 5.5.

TABLE 7

| Experiment | Formulation ID | Description |
|---|---|---|
| SD_1 | Form-1 | 32.5 mg/mL prot, 10 mM His, 27.5 mg/mL Suc, 0.01% PS-80, pH 5.5 |
| SD_1 | Form-5 | 16.25 mg/mL prot, 10 mM His, 27.5 mg/mL Suc, 0.01% PS-80, pH 5.5 |
| SD_1 | Form-7 | 32.5 mg/mL prot, 10 mM Cit, 27.5 mg/mL Suc, 0.01% PS-80, pH 5.5 |
| SD_2 | Form-1 | 65 mg/mL prot, 10 mM His, 55 mg/mL Suc, 0.01% PS-80, pH 5.5 |
| SD_2 | Form-2 | 32 mg/mL prot, 10 mM His, 27.5 mg/mL Man, 0.01% PS-80, pH 5.5 |
| SD_2 | Form-3 | 32 mg/mL prot, 10 mM His, 5 mg/mL Suc and 22.5 Man, 0.01% PS-80, pH 5.5 |
| SD_2 | Form-4 | 32 mg/mL prot, 10 mM His, 18 mg/mL Suc/9 mg/mL Met, 0.01% PS-80, pH 5.5 |
| SD_2 | Form-5 | 16 mg/mL prot, 10 mM His, 27.5 mg/mL Suc, 0.01% PS-80, pH 5.5 |
| SD_2 | Form-6 | 32 mg/mL prot, 5 mM His/5 mM Cit, 27.5 mg/mL Suc, 0.01% PS-80, pH 5.5 |
| SD_2 | Form-7 | 32 mg/mL prot, 10 mM Cit, 27.5 mg/mL Suc, 0.01% PS-80, pH 5.5 |
| SD_2 | Form-8 | 32 mg/mL prot, 10 mM Cit, 0.01% PS-80, pH 5.5 |
| SD_2 | Form-9 | 32 mg/mL prot, 10 mM Cit, 13.8 mg/mL Suc, 0.01% PS-80, pH 5.5 |
| lyo | 1 | 65 mg/ml prot, 10 mM His, 55 mg/ml Suc, 0.01% PS-80, pH 5.5 |
| lyo | 2 | 32 mg/ml prot, 10 mM His, 27.5 mg/ml Suc, 0.01% PS-80 |
| lyo | 3 | 16 mg/ml prot, 10 mM His, 27.5 mg/ml Suc, 0.01% PS-80 |
| lyo | 4 | 16 mg/ml prot, 10 mM His, 32.5 mg/ml Suc, 0.01% PS-80 |
| lyo | 5 | 16 mg/ml prot, 10 mM His, 13.75 mg/ml Suc, 13.75 mg/ml Man, 0.01% PS-80 |
| lyo | 6 | 16 mg/ml prot, 10 mM His, 27.5 mg/ml Suc, 5 mg/ml Man, 0.01% PS-80 |
| lyo | 7 | 16 mg/ml prot, 10 mM His, 22.5 mg/ml Suc, 5 mg/ml Man, 0.01% PS-80 |
| lyo | 8 | 16 mg/ml prot, 10 mM His, 32 mg/ml Suc, 12 mg/ml Man, 0.01% PS-80 |
| lyo | 9 | 16 mg/ml prot, 10 mM His, 20.5 mg/ml Suc, 7 mg/ml Man, 0.01% PS-80 |
| lyo | 10 | 16 mg/ml prot, 10 mM His, 27.5 mg/ml Man, 0.01% PS-80 |
| lyo | 11 | 16 mg/ml prot, 10 mM His, 7 mg/ml Suc, 20.5 mg/ml Man, 0.01% PS-80 |
| lyo | 12 | 32 mg/ml prot, 10 mM His, 13.75 mg/ml Suc, 13.75 mg/ml Man, 0.01% PS-80 |
| lyo | 13 | 16 mg/ml prot, 27.5 mg/ml Suc, 0.01% PS-80 (self-buffered) |
| lyo | 14 | 16 mg/ml prot, 10 mM His, 27.5 mg/ml Sor, 0.01% PS-80 |
| lyo | 15 | 16 mg/ml prot, 10 mM His, 27.5 mg/ml Tre, 0.01% PS-80 |
| lyo | 16 | 16 mg/ml prot, 10 mM His, 22.5 mg/ml Suc, 5 mg/ml Sor, 0.01% PS-80 |
| lyo | 17 | 16 mg/ml prot, 10 mM His, 22.5 mg/ml Suc, 5 mg/ml Tre 0.01% PS-80 |
| lyo | 18 | 16 mg/ml prot, 10 mM His, 27.5 mg/ml Suc, 5 mg/ml Tre 0.01% PS-80 |
| lyo | 19 | 16 mg/ml prot, 10 mM His, 13.75 mg/ml Suc, 13.75 mg/ml Tre 0.01% PS-80 |
| lyo | 20 | 16 mg/ml prot, 10 mM His, 5 mg/ml Suc, 22.5 mg/ml Tre 0.01% PS-80 |
| lyo | 21 | 16 mg/ml prot, 10 mM His, 22.5 mg/ml Suc, 5 mg/ml Ile, 0.01% PS-80 |
| lyo | 22 | 16 mg/ml prot, 10 mM His, 27.5 mg/ml Suc, 5 mg/ml Ile, 0.01% PS-80 |
| lyo | 23 | 16 mg/ml prot, 10 mM His, 22.5 mg/ml Suc, 5 mg/ml Arg 0.01% PS-80 |
| lyo | 24 | 16 mg/ml prot, 10 mM His, 22.5 mg/ml Suc, 5 mg/ml Gly, 0.01% PS-80 |
| lyo | 25 | 16 mg/ml prot, 10 mM His, 22.5 mg/ml Suc, 5 mg/ml Lys, 0.01% PS-80 |
| lyo | 26 | 16 mg/ml prot, 5 mM His, 27.5 mg/ml Suc, 0.01% PS-80 |
| lyo | 27 | 16 mg/ml prot, 20 mM His, 27.5 mg/ml Suc, 0.01% PS-80 |
| lyo | 28 | 16 mg/ml prot, 40 mM His, 27.5 mg/ml Suc, 0.01% PS-80 |
| lyo | 29 | 16 mg/ml prot, 10 mM His, 27.5 mg/ml Pro, 0.01% PS-80 |
| lyo | 30 | 16 mg/ml prot, 10 mM His, 27.5 mg/ml Suc, 5 mg/ml Pro, 0.01% PS-80 |
| lyo | 31 | 16 mg/ml prot, 10 mM His, 27.5 mg/ml Suc, 0.02% PS-80 |
| lyo | 32 | 16 mg/ml prot, 10 mM His, 27.5 mg/ml Suc, 0.05% PS-80 |
| lyo | 33 | 16 mg/ml prot, 10 mM His, 27.5 mg/ml Suc, 0.1% PS-80 |
| lyo | 34 | 16 mg/ml prot, 10 mM Cit, 5 mg/ml Suc, 22.5 mg/ml Man, 0.01% PS-80 |
| lyo | 35 | 16 mg/ml prot, 5 mM His, 5 mM Cit, 5 mg/ml Suc, 22.5 mg/ml Man, 0.01% PS-80 |

TABLE 7-continued

| Experiment | Formulation ID | Description |
|---|---|---|
| lyo | 36 | 16 mg/ml prot, 10 mM Cit, 27.5 mg/ml Suc, 0.01% PS-80 |
| lyo | 37 | 16 mg/ml prot, 5 mM Cit, 27.5 mg/ml Suc, 0.01% PS-80 |
| SD_3 | Form-1 | 65 mg/ml prot, 10 mM His, 55 mg/ml Suc, 0.01% PS-80, pH 5.5 |
| SD_3 | Form-2 | 32.5 mg/ml prot, 10 mM His, 65 mg/ml Suc, 0.01% PS-80, pH 5.5 |
| SD_3 | Form-3 | 32.5 mg/ml prot, 10 mM His, 97 mg/ml Suc, 0.01% PS-80, pH 5.5 |
| SD_3 | Form-4 | 32.5 mg/ml prot, 10 mM His, 55 mg/ml Suc, 10 mg/ml Ile, 0.01% PS-80, pH 5.5 |
| SD_3 | Form-5 | 32.5 mg/ml prot, 10 mM His, 65 mg/ml Suc, 0.1% PS-80, pH 5.5 |
| SD_3 | Form-6 | 32.5 mg/ml prot, 10 mM His, 60 mg/ml Suc, 5 mg/ml Sor, 0.01% PS-80, pH 5.5 |
| SD_3 | Form-7 | 32.5 mg/ml prot, 10 mM His, 55 mg/ml Suc, 10 mg/ml Sor 0.01% PS-80, pH 5.5 |
| SD_3 | Form-8 | 32.5 mg/ml prot, 10 mM His, 55 mg/ml Tre, 10 mg/ml Sor, 0.01% PS-80, pH 5.5 |
| SD_3 | Form-9 | 32.5 mg/ml prot, 5 mM His/5 mM Cit, 65 mg/ml Suc, 0.01% PS-80, pH 5.5 |

His = histidine; Cit = citrate; Suc = sucrose, Man = mannitol; Sor = sorbitol Tre = trehalose; Ile = isoleucine; Arg = arginine; Gly = glycine; Lys = lysine Pro = proline Certain formulations shown in Table 7 were tested for stability for 0-6 months at 5° C., 25° C. or 40° C. Select formulations were suspended in non-aqueous vehicles for further studies in Example 8.

Example 8

CNTO148 Suspension Formulations

Select formulation from Example 7 were suspended at 100 mg/mL or 200 mg/mL in non-aqueous vehicles SO, EO, or EO/SO/50/50 (Table 8). Stability of both the spray-dried and the suspension formulations were tested at 0, 1, 2, 3, 4, 5, and 6 months after storage at 5° C., 25° C., or 40° C. using size exclusion HPLC (SE-HPLC), capillary SDS-PAGE, capillary isoelectric focusing (cIEF), circular dichroism (CD), or peptide mapping by mass spectrometry. Select formulations were treated with aluminium oxide to remove peroxides using standard methods. In SE-HPLC, % retainment of the main HPLC peak over time was assessed as an indicator of CNTO148 stability in the formulations.

TABLE 8

| SD Formulation | Description | Suspensions |
|---|---|---|
| Form-1 | 32.5 mg/mL protein, 10 mM Histidine, 27.5 mg/mL sucrose, 0.01% PS-80, pH 5.5 (SD at 6% total solids) | 200 mg/ml in SO<br>200 mg/ml in SO/EO<br>200 mg/ml in EO<br>100 mg/ml in SO<br>100 mg/ml in SO/EO |
| Form-5 | 16.25 mg/mL protein, 10 mM Histidine, 27.5 mg/mL sucrose, 0.01% PS-80, pH 5.5 (SD at 4.3% total solids) | 100 mg/ml in SO<br>100 mg/ml in SO/EO |
| Form-7 | 32.5 mg/mL protein, 10 mM Citrate, 27.5 mg/mL sucrose, 0.01% PS-80, pH 5.5 (SD at 6% total solids) | 200 mg/ml in SO/EO<br>200 mg/ml in EO<br>100 mg/ml in SO/EO<br>100 mg/ml in SO/EO* |

*(no peroxide removal treatment)

FIGS. 8A and 8B and FIGS. 9A and 9B show stability of select spray-dried formulations and suspensions of those in SO, EO, and SO/EO/50/50 after storage at 25° C. (FIGS. 8A and 8B) and at 40° C. (FIGS. 9A and 9B) up to 6 months as a measure of stability of the SE-HPLC main peak. Formulations appear to group together based on a spray-dried (SD) formulation type (Form-1 vs. Form-5 vs. Form-7 of experiment SD_1 in Table 7), suggesting that % loading and vehicle composition may have less of an effect on stability as assessed using SE-HPLC. Both the spray dried (SD) and suspension formulations were more stable when compared to the control aqueous formulation (101 mg/mL protein, 10 mM histidine, 4.5 mg/mL sucrose, 0.015% PS-80, pH 5.6).

CNTO148 bioactivity (inhibition of TNFα activity on cells using routine methods) was measured initially and after storage at 25° C. for up to 6 months and at 40° C. for up to 4.5 months from spray-dried and 100 mg/mL SO/EO/50/50 suspension formulations. CNTO148 bioactivity was retained after spray-drying, and in spray-dried formulations after 6 months of storage at 25° C., as well as in suspension formulations (FIG. 10).

Figure 11:
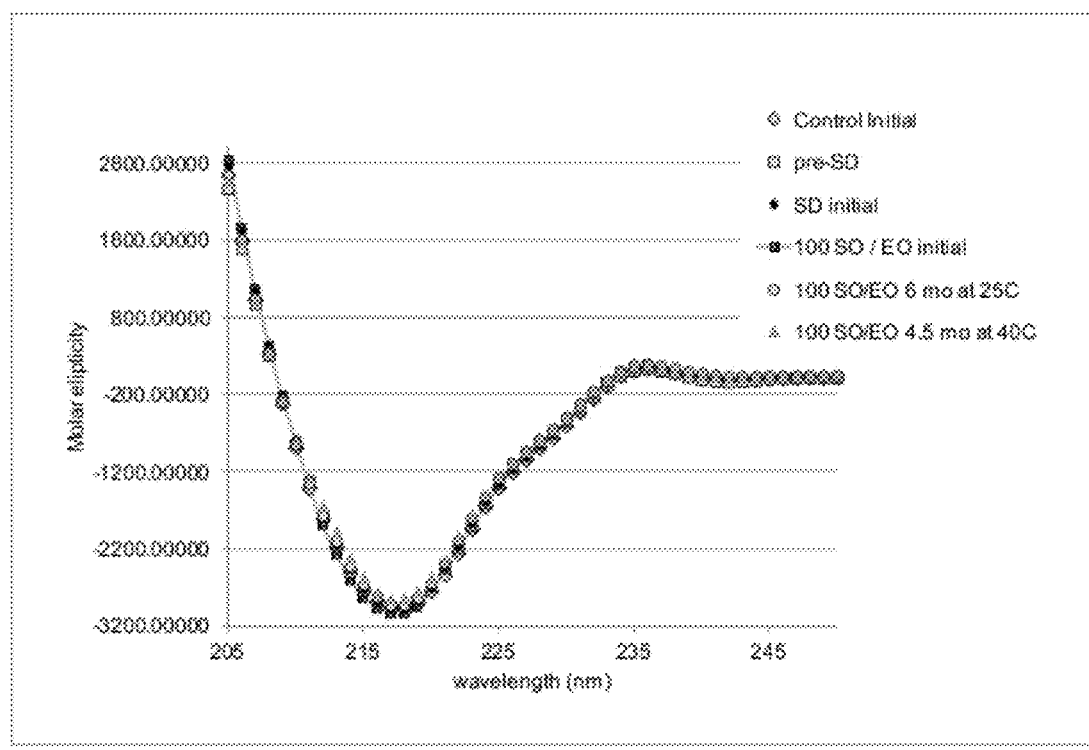
FIG. 11. Far UV CD scan of CNTO148 spray-dried Form-1 formulation of experiment SD_1 in Table 7 and Form-1 100 mg/mL suspension formulations collected at 25° C. SD=spray-dried. SO/EO=EO/SO/50/50.

Possible changes in secondary structure in both spray-dryed and suspension formulations were evaluated using far UV CD scan (FIG. 11). No changes were identified after spray drying or after storage of both spray-dried and suspension formulations.

Example 9

CNTO148 Formulations

CNTO148 was used as an anti-TNFα antibody in Examples 1-7. Additional suspension formulations of CNTO148 are made as shown in Table 9 using spray-dried particle formulations of CNTO148 described in Example 7. The resulting suspension formulations are evaluated for their stability and injectability using methods described herein.

TABLE 9

| Vehicle Composition (% v/v) | CNTO148 concentrations in vehicle (% w/w) | CNTO148 concentration mg/mL* |
|---|---|---|
| EO (100) | 10, 20, 30 50, 60 | 53.6, 107.2, 160.8, 268.0, 321.6 |
| SO/EO (5/95) | 1, 5, 10, 20, 30, 40, 50, 60 | 5.4, 26.8, 53.6, 107.2, 160.8, 214.4, 268.0, 321.6 |
| SO/EO (10/90) | 1, 5, 10, 20, 30, 40, 50, 60 | 5.4, 26.8, 53.6, 107.2, 160.8, 214.4, 268.0, 321.6 |
| SO/EO(15/85) | 1, 5, 10, 30, 40, 50, 60 | 5.4, 26.8, 53.6, 160.8, 214.4, 268.0, 321.6 |
| SO/EO(25/75) | 1, 5, 10, 30, 40, 50, 60 | 5.4, 26.8, 53.6, 160.8, 214.4, 268.0, 321.6 |
| SO/EO(30/70) | 1, 5, 10, 20, 30, 40, 50, 60 | 5.4, 26.8, 53.6, 107.2, 160.8, 214.4, 268.0, 321.6 |
| SO/EO (50/50) | 50, 60 | 268.0, 321.6 |

The invention claimed is:

1. A non-aqueous high concentration suspension formulation, consisting of:
   a. a vehicle, consisting of sesame oil as a hydrophobic agent and ethyl oleate as a viscosity-reducing agent; and
   b. an antibody formulated with an excipient.

2. The formulation of claim 1, wherein the antibody is an anti-TNFα antibody.

3. The formulation of claim 1, wherein the amount of the viscosity-reducing agent in the vehicle is between 0.2%-95% by volume (% v/v) of the vehicle.

4. The formulation of claim 2, wherein the anti-TNFα antibody is present at about 0.5%, 1%, 5%, 10%, 20%, 30%, 40%, 50% or 60% by weight (% w/w) of the formulation.

5. The formulation of claim 2, wherein the anti-TNFα antibody is spray dried or lyophilized.

6. The formulation of claim 2, wherein the anti-TNFα antibody comprises a light chain variable region (VL) of SEQ ID NO: 6 and a heavy chain variable region (VH) of SEQ ID NOs: 1 or 2, or a VL of SEQ ID NO: 7 and a VH of SEQ ID NOs: 3, 4, or 5.

7. The formulation of claim 6, wherein the anti-TNFα antibody is of IgG1/k type.

8. The formulation of claim 1, wherein the injection force of the formulation is equal to or less than 45 Newton (N), wherein the injection force is measured using a 1 mL rigid needle shield glass syringe having a 0.25 inch inside diameter, equipped with a 0.5 inch 26½ gauge needle at a 250 mm/min injection speed.

9. The formulation of claim 2 which is stable at 40° C. for at least one month.

10. The formulation of claim 2, wherein the excipient is a carbohydrate, an amino acid, a buffer, or a non-ionic surfactant.

11. The formulation of claim 10, wherein the carbohydrate is sucrose, trehalose, mannitol or sorbitol, the amino acid is histidine, isoleucine, methionine, glycine, arginine or lysine, the buffer is a histidine buffer or a citrate buffer, and the non-ionic surfactant is PS-80.

12. The formulation of claim 10, wherein the weight ratio (w/w) of the carbohydrate to the anti-TNFα antibody is between about 0-3 or about 1-2, the weight ratio of the amino acid to the anti-TNFα antibody is between about 0-2 or about 0.3-1.8, the histidine buffer concentration is about 0-40 mM or about 5-10 mM, the citrate buffer concentration is about 0-10 mM or about 5-10 mM, and the non-ionic detergent is present at about 0%-0.5% (% w/v) or about 0.01-0.1% (% w/v).

13. A suspension formulation consisting of a particle formulation of anti-TNFα antibody having a light chain variable region (VL) of SEQ ID NO: 6 and a heavy chain variable region (VH) of SEQ ID NOs: 1 or 2, or a VL of SEQ ID NO: 7 and a VH of SEQ ID NOs: 3, 4, or 5, consisting of
   a. 32.5 mg/mL of the anti-TNFα antibody, 10 mM histidine, 27.5 mg/mL sucrose, 0.01% (% w/v) PS-80;
   b. 16.25 mg/mL of the anti-TNFα antibody, 10 mM histidine, 27.5 mg/mL sucrose, 0.01% (% w/v) PS-80;
   c. 32.5 mg/mL of the anti-TNFα antibody, 10 mM citrate, 27.5 mg/mL sucrose, 0.01% (% w/v) PS-80;
   d. 32.5 mg/ml of the anti-TNFα antibody, 10 mM histidine, 55 mg/ml sucrose, 10 mg/ml isoleucine, 0.01% (% w/v) PS-80;
   e. 32.5 mg/ml of the anti-TNFα antibody, 10 mM histidine, 65 mg/ml sucrose, 0.01% (% w/v) PS-80;
   f. 32.5 mg/ml of the anti-TNFα antibody, 5 mM histidine, 5 mM citrate, 65 mg/ml sucrose, 0.01% (% w/v) PS-80;
   g. 32.5 mg/ml of the anti-TNFα antibody, 10 mM histidine, 5 mg/ml sucrose, 22.5 mg/mL mannitol, 0.01% (% w/v) PS-80;
   h. 32.5 mg/ml of the anti-TNFα antibody, 10 mM histidine, 55 mg/ml trehalose, 10 mg/ml isoleucine, 0.01% (% w/v) PS-80; or
   i. 65 mg/ml of the anti-TNFα antibody, 10 mM histidine, 55 mg/ml sucrose, 0.01% PS-80,
   wherein the formulations shown in a-i are dispersed in a non-aqueous vehicle consisting of sesame oil and ethyl oleate, wherein the amount of ethyl oleate in the vehicle is between 0.2%-95% by volume (% v/v) of the non-aqueous vehicle.

14. The suspension formulation of claim 13, wherein the amount of ethyl oleate in the vehicle is 5%, 10%, 15%, 30% or 50% (% v/v) of the non-aqueous vehicle.

15. The suspension formulation of claim 13, wherein the anti-TNFα antibody is of IgG1/k type.

* * * * *

SEQUENCE LISTING

<160> NUMBER OF SEQ ID NOS: 9

<210> SEQ ID NO 1
<211> LENGTH: 126
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ile Ile Leu Tyr Asp Gly Ser Lys Lys Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 2
<211> LENGTH: 126
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Phe Ile Leu Tyr Asp Gly Ser Asn Lys Lys Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Ser Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 3
<211> LENGTH: 126
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

```
Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
                100                 105                 110

Met Asp Val Trp Gly Gln Gly Thr Thr Val Thr Val Ser Ser
        115                 120                 125
```

<210> SEQ ID NO 4
<211> LENGTH: 126
<212> TYPE: PRT
<213> ORGANISM: Homo sapiens

<400> SEQUENCE: 4

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
                100                 105                 110

Met Asp Val Trp Gly Gln Gly Thr Thr Val Thr Val Ser Ser
        115                 120                 125
```

<210> SEQ ID NO 5
<211> LENGTH: 126
<212> TYPE: PRT
<213> ORGANISM: Homo sapiens

<400> SEQUENCE: 5

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Phe Ile Ser Tyr Asp Gly Ser Asn Lys Lys Ser Ala Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Val Phe Tyr Cys
                85                  90                  95

Ala Arg Asp Arg Gly Ile Gly Ala Gly Gly Asn Tyr Tyr Tyr Tyr Gly
                100                 105                 110
```

Met Asp Val Trp Gly Gln Gly Thr Thr Val Thr Val Ser Ser
            115                 120                 125

<210> SEQ ID NO 6
<211> LENGTH: 108
<212> TYPE: PRT
<213> ORGANISM: Homo sapiens

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 7
<211> LENGTH: 108
<212> TYPE: PRT
<213> ORGANISM: Homo sapiens

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 107
<212> TYPE: PRT
<213> ORGANISM: Homo sapiens

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

```
Pro Val Thr Lys Ser Phe Asn Arg Gly Glu Cys
            100                 105
```